United States Patent [19]

Cossement et al.

[11] Patent Number: 4,923,865
[45] Date of Patent: May 8, 1990

[54] SUBSTITUTED 1-(1H-IMIDAZOL-4-YL)ALKYL-BENZAMIDES AS ANTI-ISCHEMICS AND AS ALPHA-2-ADRENERGIC RECEPTOR AGONISTS

[75] Inventors: Eric Cossement, Brussels; Jean-Pierre Geerts, Leglise; Jean Gobert, Brussels; Philippe Michel, Brussels; Ernst Wülfert, Brussels, all of Belgium

[73] Assignee: U C B Societe Anonyme, Brussels, Belgium

[21] Appl. No.: 334,854

[22] Filed: Apr. 6, 1989

[30] Foreign Application Priority Data

Apr. 28, 1988 [GB] United Kingdom ............... 8810067

[51] Int. Cl.$^5$ ............... A61K 31/535; C07D 233/64; C07D 413/10
[52] U.S. Cl. ............... 514/235.8; 514/326; 514/397; 514/400; 544/139; 546/210; 548/335; 548/336
[58] Field of Search ............... 548/335, 336; 546/210; 544/139; 514/387, 400, 326, 235.8

[56] References Cited

PUBLICATIONS

Derwent Abstract of EP 269,599 (published 6/1/88).

*Primary Examiner*—Richard A. Schwartz
*Attorney, Agent, or Firm*—Wenderoth, Lind & Ponack

[57] ABSTRACT

New substituted 1-(1H-imidazol-4-yl)alkyl-benzamides and their salts, processes for the preparation thereof and pharmaceutical compositions.

These compounds have the formula

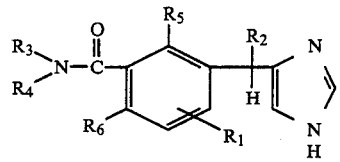

wherein
$R_1$, $R_2$=hydrogen or $C_1$–$C_4$-alkyl,
$R_3$=hydrogen, amino, hydroxyl, $C_1$–$C_4$-alkyl or $C_1$–$C_4$-hydroxyalkyl,
$R_4$=hydrogen or $C_1$–$C_4$-alkyl, or
$R_3R_4N$=pyrrolidino, piperidino or morpholino,
$R_5$ and $R_6$=hydrogen, hydroxyl, $C_1$–$C_4$-alkyl or $C_1$–$C_4$-alkoxy, at least one of
$R_5$ and $R_6$ being other than hydrogen.

These compounds are prepared either by reacting a nitrogen compound with an alkyl 1-(1H-imidazol-4-yl)alkyl-benzoate or with a 1-(1H-imidazol-4-yl)alkyl-benzoic acid, or by hydrolyzing in an acid medium a 2-hydroxy-3-[1-(1H-imidazol-4-yl)alkyl]-benzonitrile.

The compounds have anti-ischemic and $\alpha_2$-adrenoceptor agonist activities.

12 Claims, No Drawings

SUBSTITUTED 1-(1H-IMIDAZOL-4-YL)ALKYL-BENZAMIDES AS ANTI-ISCHEMICS AND AS ALPHA-2-ADRENERGIC RECEPTOR AGONISTS

The present invention relates to new substituted 1-(1H-imidazol-4-yl)alkyl-benzamides, and the non-toxic pharmaceutically acceptable acid addition salts thereof, as well as to processes for the preparation thereof and to the therapeutic use thereof.

It also relates to pharmaceutical compositions containing these new compounds.

European Pat. No. 24,829 describes 4-benzyl-1H-imidazoles, the benzyl group of which contains in the phenyl ring various substituents selected from hydrogen atoms and chloro, bromo, fluoro, methyl, ethyl, methoxy, amino, hydroxy and nitro groups. These compounds have antihypertensive, antiulcer, diuretic, sedative, analgesic, anti-inflammatory and tranquilizing properties.

European Pat. No. 58,047 describes similar 4-(phenylalkyl)-1H-imidazoles but in which the alkyl radical of the phenylalkyl group contains 1 to 6 carbon atoms; in most of the compounds, the imidazole ring is additionally substituted by an alkyl radical having 1 to 7 carbon atoms, a phenyl group or a substituted or unsubstituted benzyl radical. These compounds possess antithrombotic, antihypertensive, antimicrobial and antifungal properties.

European Pat. No. 72,615 describes also similar 4-benzyl-1H-imidazoles but in which the benzyl group is substituted in the alphaposition by an alkyl radical. The benzyl group contains in the phenyl ring various substituents selected from hydrogen and halogen atoms, methyl, ethyl, hydroxy and methoxy radicals and the methylenedioxy bridge between two adjacent carbon atoms. The pharmacological experiments described in this latter patent demonstrate that the compounds have antihypertensive, antithrombotic and diuretic properties.

U.S. patent application Ser. No. 116,325, filed Nov. 2, 1987 (now U.S. Pat. No. 4,814,343 and assigned to the assignee of the present invention) and incorporated herein by reference, describes substituted 1H-imidazoles, the most representative of which are 2-hydroxy-3-[1-(1H-imidazol-4-yl)alkyl]-benzenemethanols. These 1H-imidazoles have cardiac, cerebral and tissular anti-ischemic properties.

Continuing research work in this field, we have now synthetized new substituted 1H-imidazoles which not only have excellent cardiac, cerebral and tissular anti-ischemic properties, but also $\alpha_2$-adrenergic receptor agonist properties.

These new compounds can therefore be used, inter alia, for the prevention and treatment of disorders induced by ischemias in general. Among these disorders, angor is the clinical expression of an acute myocardial ischemia which is the result of a momentary imbalance between the myocardial oxygen demand and the oxygen supply by the coronary circulation, which desequilibrium can lead, in very severe cases, to myocardial infarction. For this reason, these compounds are especially useful for the treatment of angina pectoris and of myocardial infarction. The anti-ischemic properties of these compounds at the cerebral level allow them to be used in the prevention and treatment of functional and neurological disorders arising from cerebrovascular accidents of any origin (thrombosis and infarction), without exhibiting sedative properties, however.

In addition, various experimental observations such as measurements of the displacement of tritium labeled clonidine ([$^3$H]clonidine), carried out with preparations of $\alpha$-adrenergic receptors, and pharmacological experiments on isolated organs, lead to the conclusion that the new compounds possess a strong $\alpha_2$-adrenergic receptor agonist activity. This activity is inhibited by $\alpha$-yohimbine, which allows the compounds of the invention to be classified among the $\alpha_2$-adrenoceptor agonists. These properties are also demonstrated by the correction of the plasmatic or urinary catecholamine level increase which is due to certain pathological situations reproduced in the pharmacological models.

Consequently, the new compounds have beneficial therapeutic effects in the treatment of disorders giving rise to, or resulting from, an abnormal increase of the catecholamine levels, such as pheochromocytoma, cardiac congestion, impaired regulation of the vascular reactivity (Raynaud's disease, migraine or spasm of the coronary arteries), asthma and other atopic disorders, glaucoma, nasal congestion, headache, tension, stress, anxiety and other psychiatric disorders such as manias, depressions and memory impairments (H. J. MOTULSKY and P. A. INSEL, N. Engl. J. Med. 307, (1982), 18–29; A. DENARO et al., Acta Psychiatr. Scand. 320, (1985, Suppl. 72), 20–25). These same $\alpha_2$-adrenoceptor agonist properties enable these compounds to be used in the treatment of disorders associated with gastric and intestinal hypersecretions (J. D. DIJOSEPH et al., Life Sci. 35, (1984), 1031–1042), as well as in the treatment of the withdrawal syndromes associated with toxicomania whether the latter is of alcoholic origin or whether they result from abuse of tobacco or of opiate substances (G. LAGRUE, Rev. Prat. Médecine générale, 1987, No. 9 of 23rd November, 15–17).

Some beneficial effects of the compounds of the invention, linked with these $\alpha_2$-adrenoceptor agonist properties, may also be expected in the treatment of disorders in the metabolism of lipids and glucosides (M. C. HOUSTON et al., Clin. Res. 35, (1987, No. 1), 17A).

In addition, we have also found that these compounds possess a not insignificant diuretic, anti-inflammatory and hypotensive activity.

The new compounds according to the present invention are substituted 1-(1H-imidazol-4-yl)alkyl-benzamides having the general formula

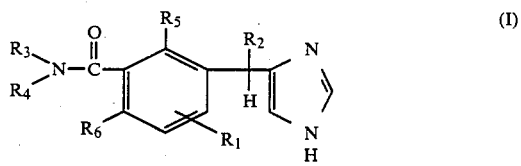

(I)

wherein $R_1$ and $R_2$, which may be the same or different, each represent a hydrogen atom or an alkyl radical, $R_3$ represents a hydrogen atom, an alkyl or hydroxyalkyl radical, an amino or hydroxyl group, $R_4$ represents a hydrogen atom or an alkyl radical, or $R_3$ and $R_4$ taken together with the nitrogen atom to which they are attached, represent a heterocyclic radical selected from the group consisting of the pyrrolidino, piperidino and morpholino radicals, and $R_5$ and $R_6$, which may be the same or different, each represent a hydrogen atom, a hydroxyl group, an alkyl or alkoxy radical, at least one of the symbols $R_5$ and $R_6$ being other than a hydrogen atom, all the alkyl and alkoxy radicals having 1 to 4 carbon atoms;

as well as the non-toxic pharmaceutically acceptable acid addition salts thereof.

When the molecule contains an asymmetric carbon atom, the compounds of formula I may be either in the form of a racemic mixture or in the form of one or other enantiomer. These various forms also fall within the scope of the present invention.

Preferred compounds according to the present invention include:

2-hydroxy-3-[(1H-imidazol-4-yl)methyl]-benzamide and the hydrochloride thereof;

2-hydroxy-3-[1-(1H-imidazol-4-yl)ethyl]-benzamide and the hydrochloride thereof;

2-hydroxy-3-[(1H-imidazol-4-yl)methyl]-N-methylbenzamide and the hydrochloride thereof;

2,6-dihydroxy-3-[(1H-imidazol-4-yl)methyl]-benzamide and the hydrochloride thereof;

2-hydroxy-3-[(1H-imidazol-4-yl)methyl]-6-methylbenzamide and the hydrochloride thereof;

2-hydroxy-5-[(1H-imidazol-4-yl)methyl]-benzamide;

2-hydroxy-3-[(1H-imidazol-4-yl)methyl]-benzohydrazide;

(+)-2-hydroxy-3-[1-(1H-imidazol-4-yl)ethyl]-benzamide and the hydrochloride thereof.

The present invention also includes the non-toxic pharmaceutically acceptable acid addition sals of the 1-(1H-imidazol-4-yl)alkyl-benzamides of formula I. Examples of pharmaceutically acceptable acids that may be mentioned include inorganic acids such as hydrochloric acid, hydrobromic acid, sulfuric acid, nitric acid and phosphoric acid and organic acids, such as acetic acid, citric acid, tartaric acid, benzoic acid, salicylic acid and maleic acid.

The substituted 1-(1H-imidazol-4-yl)alkyl-benzamides of formula I can be prepared by a general process which comprises reacting an alkyl 1-(1H-imidazol-4-yl)alkyl-benzoate of the formula

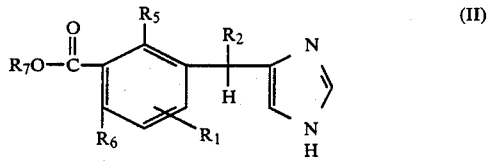

wherein $R_1$, $R_2$, $R_5$ and $R_6$ have the meanings given above and $R_7$ represents an alkyl radical having 1 to 4 carbon atoms, with a nitrogen compound of the formula

wherein $R_3$ and $R_4$ have the meanings given above.

This reaction is generally carried out under normal pressure or under a higher pressure in an autoclave, either in an alcoholic solvent such as, for example, methanol or ethanol, or in a large excess of the nitrogen compound used as starting reagent, at a temperature between ambient temperature and reflux temperature, and if necessary in the presence of sodium methoxide as a catalyst.

According to a particular embodiment, directed to the preparation of the substituted 1-(1H-imidazol-4-yl)alkyl-benzamides of formula I, in which $R_5$ and $R_6$ each represent a hydrogen atom, an alkyl or an alkoxy radical having 1 to 4 carbon atoms, at least one of the symbols $R_5$ and $R_6$ being other than a hydrogen atom, a 1-(1H-imidazol-4-yl)alkyl-benzoic acid of the formula

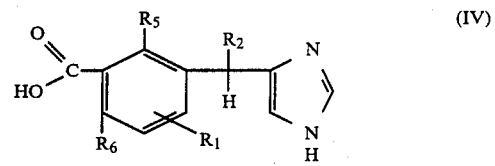

wherein $R_1$ and $R_2$ each represent a hydrogen atom or an alkyl radical having 1 to 4 carbon atoms and $R_5$ and $R_6$ have the meanings given above, is reacted with a nitrogen compound of the formula

wherein $R_3$ and $R_4$ have the meanings given above.

In order to carry out this reaction, the starting acid of formula IV is previously activated, in known manner, by means of a conventional reagent such as, for example, an alkyl haloformate, preferably ethyl chloroformate. This reaction is generally carried out at a temperature of about 0° C., in an inert solvent such as, for example, dichloromethane or acetonitrile, and in the presence of an auxiliary base such as, for example triethylamine.

According to still another embodiment, the substituted 1-(1H-imidazol-4-yl)alkyl-benzamides of formula I in which $R_1$, $R_3$ and $R_4$ are hydrogen atoms, $R_5$ represents a hydroxyl group and $R_6$ represents a hydrogen atom or an alkyl radical having 1 to 4 carbon atoms, can also be prepared by hydrolysis in an acid medium of a 2-hydroxy-3-[1-(1H-imidazol-4-yl)alkyl]-benzonitrile of the formula

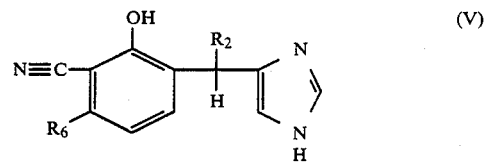

wherein $R_2$ and $R_6$ each represent a hydrogen atom or an alkyl radical having 1 to 4 carbon atoms.

This hydrolysis is generally carried out with an about 80% by volume aqueous sulfuric acid solution, at a temperature of from 60° to 75° C., for about several hours.

As an alternative, this hydrolysis can also be carried out in anhydrous methyl alcohol containing a trace of water and through which a stream of gaseous hydrogen chloride is bubbled. The intermediate imidate which is formed in situ is not isolated and is immediately converted in the amide by heating.

The non-toxic, pharmaceutically acceptable acid addition salts can be prepared from the 1-(1H-imidazol-4-yl)alkyl-benzamides of formula I by per se known methods.

The compounds of formula I in which $R_2$ is an alkyl radical and which, as a result may be in the form of a racemic mixture, can be separated into their optical enantiomers by conventional methods, either by fractional crystallization of the diastereoisomeric salts obtained by addition of an optically active acid to the racemic mixture, or by chromatography of the racemic mixture on a chiral support such as, for example, a silica on which a bovine serum albumin (BSA) is covalently grafted or an $\alpha$-glycoprotein or $\beta$-cyclodextrin containing phase. Several successive passages through the chromatography column may sometimes be necessary to improve the separation of the enantiomers.

The starting alkyl 1-(1H-imidazol-4-yl)alkyl-benzoates of formula II may be prepared by one or other of the following methods:

(a) using conventional methods, a 1-(1H-imidazol-4-yl)alkyl-benzoic acid of formula IV, in which $R_1$, $R_2$, $R_5$ and $R_6$ have the meanings given above, is esterified with an alcohol of formula $R_7OH$, in which $R_7$ represents an alkyl radical having 1 to 4 carbon atoms;

(b) when $R_5$ represents a $C_1$–$C_4$-alkoxy radical and $R_6$ a hydrogen atom, a $C_1$–$C_4$-alkyl radical or a $C_1$–$C_4$-alkoxy radical, a multi-step process can also be used which comprises (1) reacting in the presence of a base, in boiling acetone, a suitably substituted alkyl 2-hydroxybenzoate of formula VI, with a 2,3-dichloropropene of formula VII, to give an alkyl 2-(2-chloro-2-propenyloxy)-benzoate of formula VIII, according to the equation

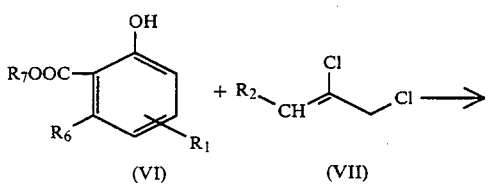

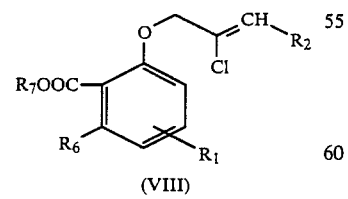

(2) heating the alkyl 2-(2-chloro-2-propenyloxy)-benzoate of formula VIII at a temperature of about 260° C., which leads via a Claisen transformation to the alkyl 3-(2-chloro-2-propenyl)-2-hydroxybenzoate of formula IX, according to the equation

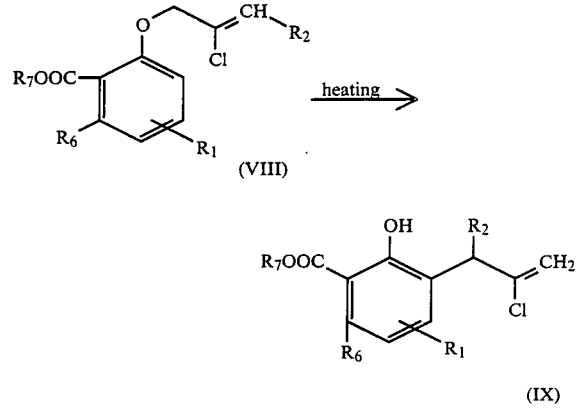

(3) alkylating the alkyl 3-(2-chloro-2-propenyl)-2-hydroxybenzoate of formula IX with a $R_8$ halide, according to the equation

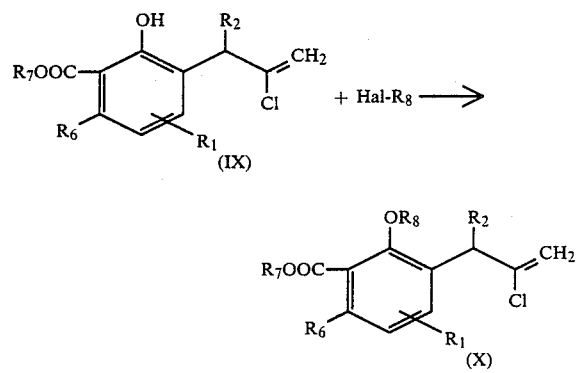

(4) oxidizing the alkyl 3-(2-chloro-2-propenyl)-2-($R_8$-oxy)-benzoate of formula X by m-chloroperbenzoic acid (mCPBA) in chloroform at reflux temperature for several hours, according to the equation

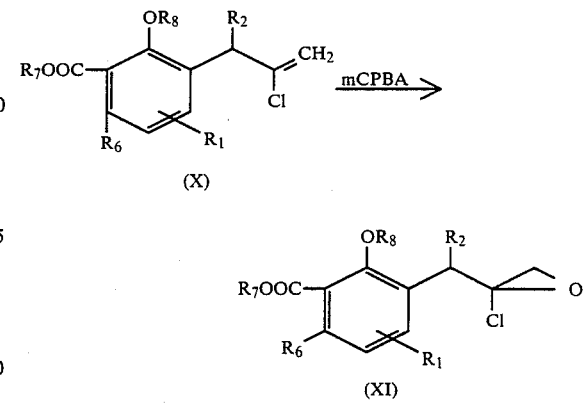

(5) reacting the epoxy ester of formula XI, in the presence of a base and at a temperature of about 60° C., with formamidine acetate, which leads to the alkyl 1-(1H-imidazol-4-yl)alkyl-benzoate of formula II, according to the equation

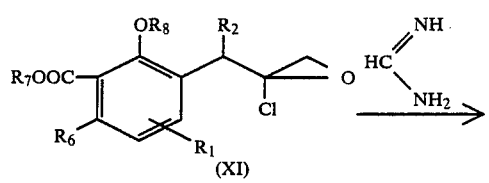

(XI)

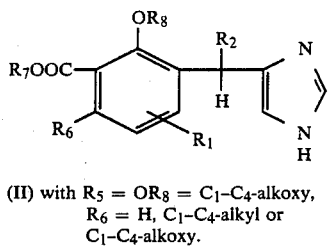

(II) with $R_5 = OR_8 = C_1-C_4$-alkoxy, $R_6 = H$, $C_1-C_4$-alkyl or $C_1-C_4$-alkoxy.

In the above formulae, $R_1$ and $R_2$ each represent a hydrogen atom or an alkyl radical having 1 to 4 carbon atoms, $R_6$ has the meaning given above, $R_7$ represents an alkyl radical having 1 to 4 carbon atoms and is preferably the methyl or ethyl radical, $R_8$ represents an alkyl radical having 1 to 4 carbon atoms and Hal is a halogen atom, preferably a chlorine or bromine atom.

(c) when $R_5$ represents a hydroxyl group and $R_6$ a hydrogen atom, a $C_1-C_4$ alkyl radical or a $C_1-C_4$ alkoxy radical, a variation of method (b) above is followed; in this variation only steps (1), (2), (4) and (5) of method (b) are carried out, the alkylation with an $R_8$ halide in step (3) being omitted. Thus the compound of formula IX which is obtained from step (2) is subjected directly to oxidation by the m-chloroperbenzoic acid.

These same esters can also be prepared from an alkyl 2-oxo-cyclohexanecarboxylate and a 4-(1-chloroalkyl)-1H-imidazole according to the multi-step process described in the above-mentioned U.S. patent application Ser. No. 116.325 (see example 4.13. hereinafter).

(d) an alkyl benzoate of formula XII is reacted with a 1H-imidazole-4-methanol of formula XIII, according to the equation

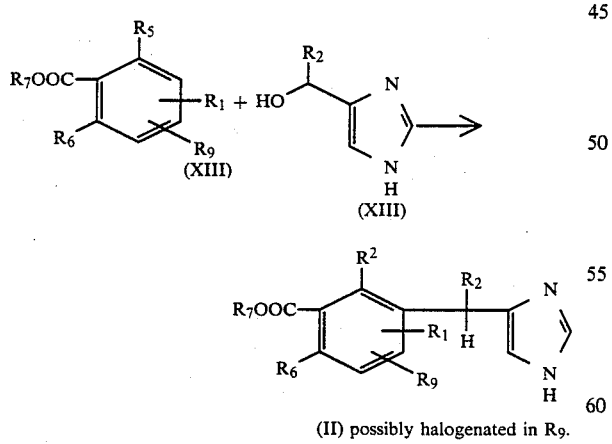

(II) possibly halogenated in $R_9$.

In these formulae, $R_1$, $R_2$, $R_5$ and $R_6$ have the meanings given above, $R_7$ represents an alkyl radical having 1 to 4 carbon atoms and $R_9$ represents a hydrogen atom or a halogen atom such as a bromine atom. This Friedel-Crafts reaction is generally carried out in an inorganic acid such as concentrated sulfuric acid or polyphosphoric acid, or in an organic acid such as formic acid or in a mixture of the aforesaid acids, for several hours at a temperature between 20° and 100° C. This process does not always result in a single compound. Indeed, a mixture of the position isomers alkyl 3-[1-(1H-imidazol-4-yl)alkyl]-benzoate and alkyl 5-[1-(1H-imidazol-4-yl)alkyl]-benzoate is sometimes obtained from which the two isomers can be separated and purified by chromatography.

Experience shows, however, that the chromatographic separation is sometimes more easily when carried out with the acids rather than with the esters. This is why, if necessary, the mixture of the isomeric esters obtained is first subjected to hydrolysis, which results in a mixture of the corresponding isomeric acids which are then separated by chormatography. These acids are subsequently re-esterified so as to provide the desired esters of formula II.

When, in the alkyl 1-(1H-imidazol-4-yl)alkyl-benzoates thus obtained, $R_9$ represents a halogen atom, this halogen atom is eliminated during a supplementary hydrogenolysis step, to give the corresponding compounds of formula II.

(e) when $R_1$ represents a hydrogen atom, $R_5$ a hydroxyl group and $R_6$ a hydrogen atom or an alkyl radical having 1 to 4 carbon atoms, a multi-step process can also be used, which includes:

(1) reacting, in the presence of sodium ethoxide, a 4-(1-chloroalkyl)-1H-imidzole of formula XIV with two equivalents of an alkyl (preferably ethyl) 4-hydroxy-3-oxo-butanoate of formula XV, the hydroxyl function of which is protected, to give an alkyl 4-hydroxy-2-[1-(1H-imidazol-4-yl)alkyl]-3-oxo-butanoate of formula XVI, according to the equation

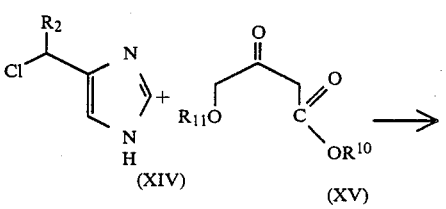

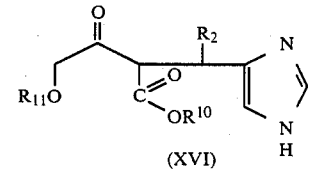

(2) reducing the beta-ketoester of formula XVI into the beta-hydroxyester of formula XVII with sodium borohydride, according to the equation

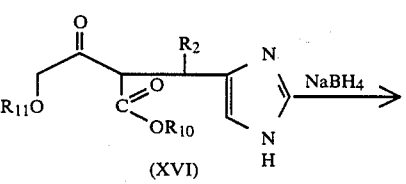

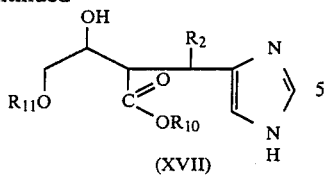

(XVII)

(3) simultaneously deprotecting and cyclizing by means of known methods, the beta-hydroxyester of formula XVII to give a 4-hydroxy-3-[1-(1H-imidazol-4-yl)alkyl]-dihydro-2(3H)-furanone of formula XVIII, according to the equation

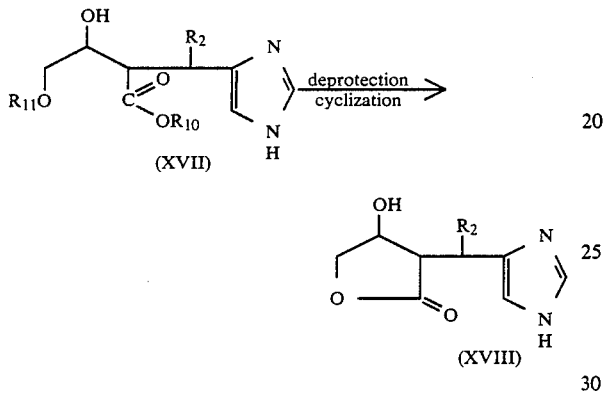

(4) thermal dehydration of the 4-hydroxy-3-[1-(1H-imidazol-4-yl)alkyl]-dihydro-2(3H)-furanone of formula XVIII by heating at a high temperature and under reduced pressure to give a 3-[1-(1H-imidazol-4-yl)alkyl]-2(5H)-furanone of formula XIX, according to the equation

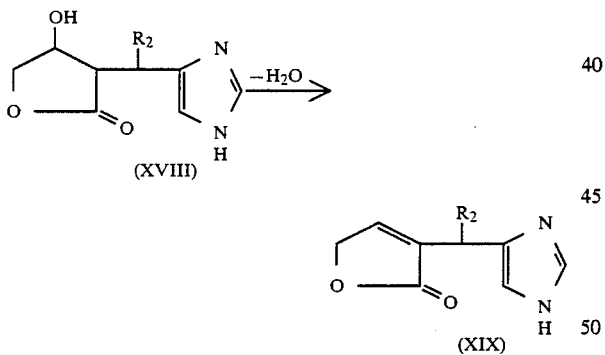

This dehydration can also be carried out by heating in a high boiling inert solvent such as, for example, ethylene glycol.

(5) subjecting to a cycloaddition reaction the 3-[1-(1H-imidazol-4-yl)alkyl]-2(5H)-furanone of formula XIX with an alkyl acrylate of formula XX, which results in the alkyl 1-(1H-imidazol-4-yl)alkylbenzoate of formula II, according to the equation

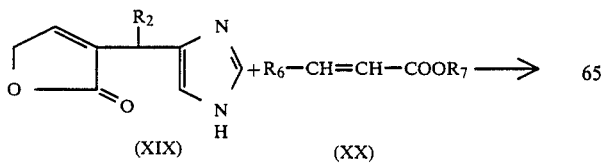

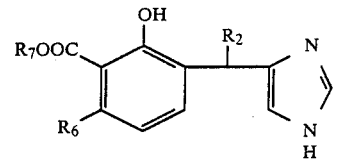

(II) with $R_1$ = H
$R_5$ = OH
$R_6$ = H or $C_1$-$C_4$-alkyl.

This Diels-Alder reaction is first of all carried out in the presence of triethylamine and of trimethylchlorosilane whereby the 2(5H)-furanone of formula XIX is converted into the corresponding 2-trimethylsilyloxyfuran (diene). When the reaction of this silylated intermediate compound with the alkyl acrylate is complete, the primary adduct (an oxanorbornene) is hydrolyzed and aromatized into the alkyl hydroxybenzoate of formula II by heating in concentrated hydrochloric or hydrobromic acid for several minutes.

In these formulae, $R_2$ represents a hydrogen atom or an alkyl radical having 1 to 4 carbon atoms, $R_6$ has the meaning given above, $R_7$ and $R_{10}$ each represent an alkyl radical having 1 to 4 carbon atoms, preferably the methyl or ethyl radical, and $R_{11}$ represents a conventional protecting group selected from the methyl, tert-butyl, benzyl and benzoyl radicals, the benzyl radical being preferred.

The 4-(1-chloroalkyl)-1H-imidazoles of formula XIV can be prepared from the corresponding 1H-imidazole-4-methanols by chlorination according to known methods (J. L. KELLEY et al., J. Med. Chem. 40, (1977), 721-723).

The alkyl 4-hydroxy-3-oxo-butanoates of formula XV, the hydroxyl function of which is protected by the $R_{11}$ radical can be prepared from the corresponding ethyl 4-chloro-3-oxo-butanoates according to the method described by T. MEUL et al., Chimia, 41, (1987), 73-76.

The 1-(1H-imidazol-4-yl)alkyl-benzoic acids of formula IV used as starting materials, either for the preparation of the alkyl 1-(1H-imidazol-4-yl)alkyl-benzoates of formula II by method (a) above, or for preparation of the compounds of formula I, can be obtained by one or other of the following methods:

(1) oxidation of the corresponding 1-(1H-imidazol-4-yl)alkyl-benzenemethanols of formula XXI, according to the equation

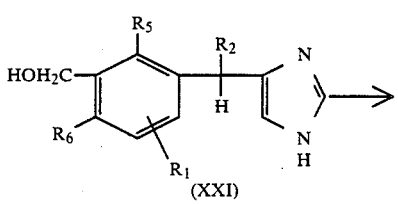

-continued

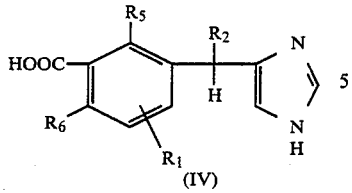

In these formulae, $R_1$, $R_2$, $R_5$ and $R_6$ have the meanings given above. This oxidation reaction is carried out by heating the starting alcohol up to 170° to 190° C. for several hours, in molten potassium hydroxide. The acid is isolated after the reaction mixture has been dissolved in water and after acidification of the aqueous solution of the potassium salt of the acid. The preparation of the alcohols of formula XXI used as starting materials in this reaction is described in the above-mentioned U.S. patent application Ser. No. 116,325.

(2) hydrolysis, using conventional methods, of the corresponding esters prepared by one of the methods (b), (c), (d) or (e) described above. When starting from a mixture of the isomeric esters prepared according to method (d), the mixture of the resulting isomeric acids is subjected to chromatography so as to separate the individual acids.

The starting 2-hydroxy-3-[1-(1H-imidazol-4-yl)alkyl]-benzonitriles of formula V can be prepared beginning with steps (1) to (4) of method (e) used in the preparation of the esters of formula II described above, to give the 3-[1-(1H-imidazol-4-yl)alkyl]-2(5H)-furanone of formula XIX, which compound is then further reacted with an acrylonitrile of formula XXII, according to the equation

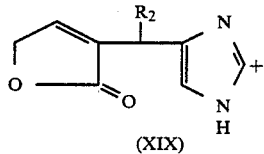

This cycloaddition reaction is carried out under the same conditions as those which are described above for step (5) of method (e).

In these formulae, $R_2$ and $R_6$ each represent a hydrogen atom or an alkyl radical having 1 to 4 carbon atoms.

As already mentioned above, the substituted 1-(1H-imidazol-4-yl)alkyl-benzamides of formula I, and their non-toxic pharmaceutically acceptable acid addition salts possess valuable pharmacological properties. In particular, it has been found that they have excellent cardiac and cerebral anti-ischemic properties, as well as $\alpha_2$-adrenoceptor agonist properties.

The pharmacological tests described below demonstrate these various properties.

The following compounds according to the present invention have been subjected to the pharmacological tests:
2-hydroxyl-3-[(1H-imidazol-4-yl)methyl]-benzamide hydrochloride (compound A),
2-hydroxy-3-[1-(1H-imidazol-4-yl)ethyl]-benzamide hydrochloride (compound B),
2-hydroxy-3-[(1H-imidazol-4-yl)methyl]-N-methylbenzamide hydrochloride (compound C),
2-hydroxy-3-[(1H-imidazol-4-yl)methyl]-benzohydrazide (compound D),
2-hydroxy-N-(2-hydroxyethyl)-3-[(1H-imidazol-4-yl)methyl]-benzamide hydrochloride (compound E),
3-[(1H-imidazol-4-yl)methyl]-2-methoxybenzamide hydrochloride (compound F),
2-hydroxy-5-[(1H-imidazol-4-yl)methyl]-benzamide (compound G),
2-hydroxy-3-[(1H-imidazol-4-yl)methyl]-N,N-dimethylbenzamide (compound H),
2,6-dihydroxy-3-[(1H-imidazol-4-yl)methyl]-benzamide hydrochloride (compound I),
5-tert-butyl-2-hydroxy-3-[(1H-imidazol-4-yl)methyl]-benzamide (compound J),
2-hydroxy-3-[(1H-imidazol-4-yl)methyl]-6-methylbenzamide hydrochloride (compound K),
2-hydroxy-3-[(1H-imidazol-4-yl)methyl]-4-methylbenzamide (compound L),
N,2-dihydroxy-3-[(1H-imidazol-4-yl)methyl]-benzamide hydrochloride (compound M),
2,6-dihydroxy-3-[1-(1H-imidazol-4-yl)ethyl]-benzamide hydrochloride (compound N),
6-hydroxy-3-[(1H-imidazol-4-yl)methyl]-2-methylbenzamide hydrochloride (compound O),
(+)-2-hydroxy-3-[1-(1H-imidazol-4-yl)ethyl]-benzamide hydrochloride (compound P).

1. Cardiac anti-ischemic activity.

(a) Artificially induced acute coronary insufficiency in an awake dog. In an awake dog (suitably equipped with a pneumatic occluder around the inferior descending coronary artery and with intracardiac electrodes), an occlusion of the coronary artery is obtained by the pneumatic occluder for a period of six minutes. Because of the reduction in the oxygen supply which results from this, the occlusion produces myocardial ischemia which is expressed on the electrocardiogram by a reproducible and quantifiable ST-segment elevation. The anti-ischemic action of a compound results in a reduction of the magnitude of the ST-segment elevation. (P. R. MAROKO and E. BRAUNWALD, Circulation, 53, (1976, Suppl. I), 162–168; S. E. EPSTEIN et al., Circulation, 53, (1976, Suppl. I), 191–197).

Table I shows, for the compounds submitted to the test, the dose ($DE_{20}$ Table I shows, for the compounds submitted to the test, the dose ($DE_{20}$ in $\mu$mole/kg) which, when administered intravenously to groups of ten animals, produces a mean reduction of at least 20% of the ST-segment elevation on the whole group of animals. As a reference compound, 1-(isopropylamino)-3-(1-naphthyloxy)-2-propanol (or propranolol) is used.

TABLE I.

| Test Compound | $DE_{20}$ (in $\mu$moles/kg) |
|---|---|
| A | 0.03 |
| B | 0.02 |
| C | 0.3 |

TABLE I.-continued

| Test Compound | DE$_{20}$ (in μmoles/kg) |
|---|---|
| D | 3 |
| E | <3 |
| F | <3 |
| G | <1 |
| I | 0.32 |
| K | 0.32 |
| propranolol | 2 |

From this table, it is evident that the compounds of the invention display substantial anti-ischemic activity.

(b) Effort trial on a moving belt. In this test, a group of at least four dogs is used (equipped with intracardiac electrodes), the dogs having an organic stenosis at the level of a coronary artery. This stenosis causes imbalance between the demand and supply of oxygen when the animal is required to make an effort. This imbalance is expressed on the electrocardiogram by an increase in the ST-segment.

In the trial, the dog runs at a speed of 12 km/h on a moving belt having a slope of 15°. This maximum effort is required for one minute. During the trial, the increase in the ST-segment is recorded, together with the natural increase in the pulse rate. The experiment is repeated at least four times, and the mean of the values obtained is taken as reference (100%) for the group of animals. The animals are then allowed to rest for a minimum of 24 hours before being subjected to a new effort trial under the influence of the compound to be studied.

The compound to be studied is administered slowly (over 1 minute) by intravenous injection 5 minutes before the new effort trial. In the course of the latter, the variations in the same parameters are recorded. Table II shows the mean reduction observed for the ST-segment (in %) at the indicated dose (μmole/kg) and for the pulse rate (in beats per minute), with respect to the reference values obtained in the first trial.

TABLE II

| | Maximum effort at 12 Km/h for 1 minute. | | |
|---|---|---|---|
| Compound | dose (μmole/kg) | reduction in ST-segment (in %) | reduction in the pulse rate (in beats/min.) |
| A | 0.018 | 74 | 3 |
| C | 0.32 | 50 | 1 |
| pro pranolol | 1.0 | 74 | 35 |

From this table, it can be seen that the compounds of the invention have a good anti-ischemic activity demonstrated by a high reduction in the ST-segment, which is also found with propranolol, but only at a much higher dose. In addition, unlike the propranolol which causes at the same time a large reduction in cardiac rhythm during the trial, which is not desirable and which is detrimental to the maintenance of the effort, the compounds of the invention are not inimical to the natural increase in pulse rate during the effort. They thus allow the pulse rate to adapt correctly to the effort, while at the same time opposing to the ischemia.

2. Cerebral anti-ischemic activity.

(a) General and permanent cerebral ischemia in rat. Male Wistar rats (200 to 250 g) are anesthetized by inhalation of halothane (1 to 5%) contained in a $N_2O$—$O_2$ (70:30) mixture. The two common carotid arteries are ligatured simultaneously close to the passage between the internal carotid and external carotid using the method described by M. LE PONCIN-LAFITTE et al., J. Pharmacol. (Paris), 14, (1983), 99–102.

The compound to be tested is administered intraperitoneally for a first time 30 minutes before making the ligatures, and subsequently 30 minutes and 270 minutes after making the ligatures. On the next day, and on the day after the next, the neurological deficit in the surviving animals is evaluated by the method described by C. CAPDEVILLE et al., J. Pharmacol. (Paris), 15, (1984), 231–237, and by B. KOLB et al., Neurobehav. Toxicol. Teratol. 7, (1985), 71–78. The sensorimotor functions taken into consideration during this evaluation are spontaneous motility, grasping reflex, placing reactions both visual and by loss of support, paw-flexion reflex, the righting reflex and the test of tail hanging. The maximum possible score for an animal not having an ischemia is 17. Table III gives for compound A, administered intraperitoneally at a dose of 0.76 μg/kg (3.2 nmoles), the mean of the neurological scores determined for the whole group of surviving animals of the control group and of the treated group, as recorded two days after the ligatures. The statistical significance (P) of the difference observed between these mean values is evaluated by the Mann-Whitney test.

TABLE III

| Neurological scores after 2 days. | |
|---|---|
| control (n = 16) | 12 |
| A (n = 15) | 15 |
| (P) | (0.005) | n = number of surviving animals.

It is seen from this Table that compound A, at a very small dose, significantly reduces in the treated animals the neurological deficit caused by ischemia.

(b) Unilateral, multifocal cerebral ischemia in the rat. In awake, male Sprague-Dawley SPF rats, aged from 8 to 9 months, a permanent, unilateral cerebral ischemia (or embolization) is caused by introduction of 2000 microspheres (provided by 3M, St. Paul, U.S.A.; diameter 58±2 μm) into the right carotid stream (A. M. BRALET et al., Stroke, 10, (1979), 34–38; M. LE PONCIN-LAFITTE et al., Pathol. Biol. (Paris), 30, (1982), 289–293) after the permanent ligature of the right pterygopalatine artery (Y. KIYOTA et al., Pharmacol. Biochem. Behav. 24, (1986), 687–692).

The compound to be studied is administered for the first time 30 minutes before, and for the second time 30 minutes after embolization, while the control animals receive only a physiological salt solution. The animals are then allowed to rest. After 6 days of recovery, the surviving animals are measured for:

(1) the residual neurological deficit obtained from the test of posture and gait of the animals (Test A, maximum score: 4 points). This test evaluates:
  (a) abnormal positioning of the hind paws (S. IRWIN, Psychophamacologia (Berlin), 13, (1968), 222–257);

(b) contralateral inclination of the body during locomotion;

(c) homolateral longitudinal flexion of the body, and (d) abnormal gait (B. KOLB et al., loc. cit.).

(2) The sensorimotor functions (spontaneous motility, grasping reflex, placing reactions both visual and by loss of support (Test B, maximum score: 10 points); (C. CAPDEVILLE et al., loc. cit.).

(3) The lateralized sensorimotor response (on the contralateral side) (Test C, maximum score: 3 points). This is evaluated by combining the measurements of visual placing reflex, head orientation relfex towards a lateral sensory stimulus, and the cutaneous plantar reflex (C. CAPDEVILLE et al., loc. cit.; J. F. MARSHALL et al., Science (Washington), 174, (1971), 523–525).

(4) Tactile extinction on the left side (Test D, maximum score: 300 points). By contrast with the other tests mentioned above, for which the deficit is lower when the score is higher, the deficit is here more pronounced when the score approaches 300 (T. SCHALLERT et al., Pharmacol. Biochem. Behav. 16, (1982), 455–462).

On the seventh day of recovery, the edema present in various ipsilateral cerebral structures is also measured (M. LE PONCIN-LAFITTE et al., loc. cit.). Table IV gives the results obtained in tests A to D for compound A, administered intraperitoneally at the dose of 0.76 μg/kg (3.2 nmoles/kg), i.e. The mean of the neurological scores determined for the whole group of surviving animals of the control group and of the treated group after 6 days of recovery. Also indicated in the Table is the mean variation (in g) of body weight measured on the 7th day of recovery. The statistical significant (P) of the difference between the mean values calculated for the control animals and for the treated animals is evaluated by the Mann-Whitney test. Table IV shows that compound A significantly reduces the neurological and behavioral deficit caused by ischemia and improves the ponderal evolution of the treated animals.

TABLE IV

Mean neurological scores 6 days after embolization

| group | n (*) | test A | test B | test C | test D | weight variation (in g) |
|---|---|---|---|---|---|---|
| control | 18 | 1.0 | 7.3 | 1.0 | 243 | −5.7 |
| treated | 17 | 2.0 | 8.0 | 2.0 | 96 | +0.8 |
| (P) | | (<0.01) | (<0.05) | (<0.005) | (<0.05) | (<0.05) |

(*): n indicates the number of surviving animals in each group.

In Table V, the quantity of water (as an average of the percentage) retained in various ipsilateral cerebral structures in the control animals and in the treated animals surviving at the 7th day after embolization, is indicated. The results obtained show that treatment by compound A significantly reduces the ipsilateral edema in the different cerebral structures studied.

TABLE V

| group | n(*) | Quantity of water in various ipsilateral cerebral structures (average %) | | | |
|---|---|---|---|---|---|
| | | Hippocampus | Corpus striatum | Diencephalon | Cortex |
| control | 18 | 80.20 | 81.57 | 77.04 | 81.33 |
| treated | 17 | 79.79 | 80.05 | 76.32 | 80.36 |
| (P) | | (<0.05) | (<0.005) | (<0.05) | (<0.01) |

(*): n indicates the number of surviving animals in each group.

3. $\alpha_2$-adrenergic agonist property.

(a) Competitive binding assay with a radioligand. The object of competitive binding assays is to measure the affinity of the compounds of the invention for $\alpha_2$-adrenoceptors. These conventional experiments involve the competition for binding to $\alpha_2$-adrenergic receptors between the tested compound on the one hand, and on the other hand, a radioligand which, in this particular case of $\alpha_2$-adrenergic receptors, is the [$^3$H]clonidine which is known to be a specific $\alpha_2$-adrenergic agonist.

The method used is that of D. C. U'PRICHARD et al., Mol. Pharmacol. 13, (1977), 454–473.

The displacement curves for binding of [$^3$H]clonidine have been determined with nine concentrations of compound A, ranging from $10^{-4}$ to $10^{-10}$ mole/l, and with three different preparations of rat brain membranes. The samples were incubated for 30 minutes, and then filtered under reduced pressure using a Whatman GF/B filter. The filters are washed three times with 5 ml of Tris-HCl buffer (pH 7.5 at 0° C.) and then dried for one minute. The radioactivity is measured in an Econofluor (-NEN Corp.) medium. The [$^3$H]clonidine (25.5 Ci/mmole) used is provided by Amersham.

The affinity of compound A for the $\alpha_2$-adrenergic receptors has been calculated from the displacement curves of the [$^3$H]clonidine. It is expressed by the concentration (IC$_{50}$ in mole/l) of compound A that is necessary to obtain a 50% inhibition of the binding of the radioligand to the receptors. The results obtained show that the compound A has a considerable affinity for the $\alpha_2$-adrenergic receptors:

$IC_{50} = 8.90 \pm 0.72 \times 10^{-9}$ mole/l (b) Stimulation of the isolated guinea-pig atria. The release of noradrenalin at the level of the nerve endings is mediated by a feedback regulating mechanism through the presynaptic $\alpha_2$-adrenergic receptors. This mechanism has been demonstrated on the guinea-pig atria by M. J. RAND et al., "Central action drugs in blood pressure regulation", 1975, 94–132. Ed. D. S. DAVIES, J. L. REID, Pitman, London.

The electrical stimulation of the isolated guinea-pig atria induces a release of noradrenalin which results in an increase in the rate of the heart beat (tachycardia). This tachycardia is inhibited by an $\alpha_2$-agonist such as, for example, clonidine, in a proportion which depends on the dose of the agonist used. The action of the $\alpha_2$-agonist may be limited in the presence of an $\alpha_2$-specific antagonist such as $\alpha$-yohimbine.

The in vitro activity of the compounds of the invention on the presynaptic $\alpha_2$-adrenergic receptors has been studied on the isolated guinea-pig atria, electrically stimulated according to the method described by I. C. MEDGETT et al., Naunyn-Schmiedeberg's Arch. Pharmacol. 304, (1978), 215-221. The compound to be studied is tested in increasing concentrations ranging from $10^{-10}$ to $10^{-3}$ mole/l. The concentration ($IC_{30}$ in mole/l) which causes a 30% reduction in the maximum tachycardia obtained initially during the electrical stimulation of the atria in the absence of the compound to be tested, is determined.

Table VI shows the $IC_{30}$ concentrations (in mole/l) obtained for the compounds of the invention as well as for clonidine.

TABLE VI.

| | Reduction in tachycardia. | |
|---|---|---|
| compound | n(*) | $IC_{30}$ (in mole/l) |
| A | 7 | $9 \times 10^{-10}$ |
| B | 6 | $7.5 \times 10^{-10}$ |
| C | 3 | $1.3 \times 10^{-7}$ |
| D | 5 | $2.2 \times 10^{-7}$ |
| F | 8 | $7 \times 10^{-8}$ |
| clonidine | 6 | $3.2 \times 10^{-9}$ |

(*) n = number of tests.

This Table shows that the compounds of the invention, in very small concentrations, oppose the tachycardia which is induced by electrical stimulation. On the other hand, in the presence of a concentration of $10^{-6}$ mole/l of α-yohimbine, the concentration of compound A necessary to obtain a reduction of 30% in the tachycardia is greater than $10^{-7}$ mole/l. These results clearly show that the compounds of the invention act through a specific mechanism via an $\alpha_2$-agonist action.

(c) Stimulation of a guinea-pig ileum. Longitudinal muscles strips attached to an isometric strain gauge are suspended in Tyrode's solution and are stretched under a tension of 1 g (G. M. DREW. Brit. J. Pharmacol. 64, (1978), 293-300; M. ANDREJAK et al., Naunyn-Schmiedelberg's Arch. Pharmacol. 314, (1980), 83-87).

Electrical stimulation of the parasympathetic nerves associated with the ileum fragments causes a contraction of the muscle. This contraction is reduced in the presence of a presynaptic $\alpha_2$-agonist and the magnitude by which the contraction is reduced depends on the concentration of the agonist used. This effect is antagonized by the simultaneous presence of an $\alpha_2$-antagonist such as α-yohimbine. The compounds to be studied have been tested at increasing concentrations ranging from $10^{-10}$ to $10^{-3}$ mole/l.

The concentration ($IC_{50}$ in mole/l) that reduces by 50% the intensity of the contraction of the muscle is determined.

Table VII gives the $IC_{50}$ concentrations (in mole/l) obtained for the compounds of the invention. These results show that these compounds are highly active at very low concentration.

TABLE VII.

| Inhibition of the contraction of guinea-pig ileum. | | |
|---|---|---|
| compound | n(*) | $IC_{50}$ (en mole/l) |
| A | 5 | $7 \times 10^{-9}$ |
| B | 6 | $3 \times 10^{-9}$ |
| E | 3 | $6 \times 10^{-5}$ |
| F | 4 | $7 \times 10^{-5}$ |
| I | 7 | $3 \times 10^{-7}$ |
| J | 4 | $3 \times 10^{-5}$ |

TABLE VII.-continued

| Inhibition of the contraction of guinea-pig ileum. | | |
|---|---|---|
| compound | n(*) | $IC_{50}$ (en mole/l) |
| L | 6 | $3 \times 10^{-8}$ |
| M | 5 | $4 \times 10^{-7}$ |
| P | 6 | $2 \times 10^{-9}$ |
| clonidine | 4 | $2 \times 10^{-8}$ |

(*) n = number of tests.

In the presence of α-yohimbine at a concentration of $10^{-6}$ mole/l, the concentration of the compounds A or B, for example, that is required for reducing muscle contraction intensity by 50% is higher, and becomes greater than $10^{-6}$ mole/l, which gives additional confirmation that the compounds of the invention act really at the level of the presynaptic $\alpha_2$-adrenergic receptors.

4. Diuretic activity. The diuretic activity of the compounds of the invention has been determined using beagle dogs (6 males and 6 females) be means of a 6-way randomized cross-over study.

The compounds to be studied are administered intravenously at increasing doses: 2, 6.5, 20, 65 and 200 μg/kg. During the first three hours following the injection, the volume of urine excreted is measured. Table VIII gives for compound A the mean relative increase in % of the volume of urine excreted with respect to the group of animals which have not received the compound.

The results show that the minimum active dose that causes a statistically significant increase ($P > 0.05$) of the urine excretion is $\leq 6.5$ μg/kg for males, while for females this dose is $\leq 2$ μg/kg.

TABLE VIII.

| | Mean relative increase in urine excretion (in %). | |
|---|---|---|
| dose (μg/kg) | males (n=6) | females (n=6) |
| 2 | 25 | 74* |
| 6.5 | 122* | 291** |
| 20 | 383** | 531** |
| 65 | 345** | 804** |
| 200 | 412** | 988** |

Analysis of the variance:
*P < 0.05
**P < 0.01
n = number of animals.

5. Toxicity. The toxicity of the compounds according to the present invention has been determined in male NMRI mice by means of Irwin's test (S. IRWIN, Psychopharmacologia, 13, (1968), 222-257).

Progressive doses of the test compound are administered intraperitoneally to groups of three mice until the lethal dose is reached (dose causing the death of two out of three animals within 48 hours). In Table IX below, the lethal dose in mg/kg found for the compounds of the invention is given. It can be seen from this Table that the compounds of the invention are not very toxic.

TABLE IX.

| | Toxicity. |
|---|---|
| compound | lethal dose (in mg/kg) |
| A | 760 |
| B | 267 |
| C | 267 |
| D | 232 |
| E | 893 |
| F | 802 |

TABLE IX.-continued

| compound | Toxicity. lethal dose (in mg/kg) |
|---|---|
| G | 651 |
| H | 245 |
| I | >270 |
| K | >268 |
| L | 231 |
| M | >288 |
| N | 284 |
| O | >268 |
| P | 294 |

The pharmaceutical compositions containing the compounds according to the present invention may be administered orally, parenterally or rectally. The pharmaceutical compositions which can be used for oral administration may so solid or liquid, for example in the form of tablets (coated or uncoated), pills, dragees, gelatine capsules, solutions, syrups, and the like. Similarly, the compositions which can be used for parenteral administration are the pharmaceutical compositions known for this mode of administration, for example aqueous or oily solutions, suspensions or emulsions. For rectal administration, the compositions containing the compounds of the invention are generally used in the form of suppositories.

The pharmaceutical forms such as injectable solutions, injectable suspensions, tablets, drops, suppositories and the like are prepared by the methods currently used by pharmacists. The compounds of the invention are mixed with a solid or liquid, non-toxic, pharmaceutically acceptable carrier, and optionally with a dispersing agent, a disintegrating agent, a stabilizing agent and the like. If desired, sweetening and coloring agents and the like may also be added.

The percentage of active compound in the pharmaceutical compositions may vary within very wide limits, according to the patient and the mode of administration, and in particular according to the frequency of administration. As far as the daily posology is concerned, it may vary within a very wide range of dosage units, for example from 3 to 350 μg of active compound once or twice a day by intravenous injection, or again from 50 μg to 5 mg of active compound once or twice a day by oral administration. By way of non-limiting example of a composition containing a compound of the invention, there are given below (a) an example of a sterile solution for intravenous administration

| Active compound | 250 μg |
|---|---|
| Sodium acetate | 19.15 mg |
| Acetic acid | 3.59 mg |
| Sodium chloride | 81 mg |
| Sterile water | ad 10 ml |

(to be kept in a 10 ml brown ampule, after sterile filtration of the solution).

(b) an example of a formula for a tablet:

| Active compound | 0.5 mg |
|---|---|
| Corn starch | 38 mg |
| Lactose | 63 mg |
| Magnesium stearate | 1.2 mg |
| Polyvinylpyrrolidone | 2.5 mg |

The following non-limiting examples are given for the purpose of illustrating the preparation of the substituted 1-(1H-imidazol-4-yl)alkylbenzamides according to the invention as well as the preparation of their intermediates. In these examples, the nuclear magnetic resonance spectra (NMR) were determined with a Bruker apparatus at 250 MHz, using tetramethylsilane as internal reference. The chemical shifts are indicated in delta (ppm). The letters s, d, dd, t, q and m indicate respectively a singlet, a doublet, a double doublet, a triplet, a quartet and a multiplet.

EXAMPLE 1. PREPARATION OF THE STARTING ALKYL 1-(1H-IMIDAZOL-4-YL)ALKYLBENZOATES OF FORMULA II.

A. By esterification of the corresponding acids (method (a)).

1. Ethyl 2-hydroxy-5-[(1H-imidazol-4-yl)methyl]-benzoate hydrochloride. A suspension of 3.1 g (12.2 mmoles) of 2-hydroxy-5-[(1H-imidazol-4-yl)methyl]-benzoic acid hydrochloride (prepared as described hereinafter in Example 2.C.) in 150 ml of absolute ethanol is saturated at 0° C. with a current of gaseous hydrochloric acid. This is then slowly heated to reflux temperature which is maintained for 10 hours. Subsequently, the solvent is evaporated until the ester precipitates. The latter is filtered, washed with diethyl ether, and then dried. 2.3 g of ethyl 2-hydroxy-5-[(1H-imidazol-4-yl)methyl]benzoate hydrochloride are obtained.
Yield: 68%. M.P.: 195°–198° C.
NMR (DMSO): delta 1.34(3H,t), 4.03(2H,s), 4.37(2H,q), 6.95(1H,d), 7.40(1H,s), 7.49(1H,dd), 8.70(1H,d), 9.12(1H,s), 10.6(1H,s).

2. Ethyl 2-hydroxy-3-[1-(1H-imidazol-4-yl)ethyl]-benzoate. This compound is prepared as described in 1. above, but starting from 2-hydroxy-3-[1-(1H-imidazol-4-yl)ethyl]-benzoic acid (prepared as described hereinafter in Example 2.A.2.). When the reaction is complete, the reaction medium is neutralized by the addition of a concentrated ammonia solution, the mineral salts are filtered off and the filtrate is evaporated under reduced pressure. The residue obtained is purified by chromatography on silica gel (eluent 8:2 v/v dichloromethane-methanol). Ethyl 2-hydroxy-3-[1-(1H-imidazol-4-yl)ethyl]-benzoate is obtained with a 35% yield. The corresponding hydrochloride melts at 168° C. (ethanol ether).

| Analysis for $C_{14}H_{16}N_2O_3 \cdot HCl$ in %: | | | |
|---|---|---|---|
| calc.: | C 56.66 | H 5.40 | N 9.44 |
| found: | 56.58 | 5.50 | 9.21 |

3. Ethyl 2-hydroxy-3-[1-(1H-imidazol-4-yl)pentyl]-benzoate. 1.18 g (3.8 mmoles) of 2-hydroxy-3-[1-(1H-imidazol-4-yl)pentyl]-benzoic acid hydrochloride (prepared as described hereinafter in Example 2.A.3.) dissolved in 15 ml of triethyl orthoformate, in the presence of 1.2 g of anhydrous montmorillonite K10, is heated to reflux temperature. Then, the mixture is filtered and evaporated under reduced pressure. The residue obtained is purified by chromatography on 150 g of silica (eluent: 95:5:0.5 v/v/v dichloromethane-methanol-ammonia). 0.213 g of ethyl 2-hydroxy-3-[1-(1H-imidazol-4-yl)pentyl]-benzoate is obtained.

NMR (DMSO): delta 0.81(3H,t), 1.0 to 1.29(2H,m), 1.34(3H,t), 1.77 to 2.0(2H,m), 4.31 to 4.41(3H,t+q), 677(1H,s), 6.86(1H,t), 7.46 to 7.50(2H, d+s), 7.63(1H,d).

The product obtained is used as such, without further purification, to prepare the corresponding benzamide (Example 4.15.).

4. Methyl 2-hydroxy-3-[(1H-imidazol-4-yl)methyl]-benzoate. This compound is prepared as described in 2. above, but starting from 2-hydroxy-3-[(1H-imidazol-4-yl)methyl]-benzoic acid hydrochloride (prepared as described hereinafter in Example 2.A.1.) and from methanol. M.P.: 153°–154° C.

NMR (DMSO): delta 3.87(2H,m), 3.91(3H,s), 6.77(1H,s), 6.87(1H,t), 7.45(1H,dd), 7.58(1H,s), 7.69(1H,dd), 10(1H,s).

B. via Claisen transformation (methods (b) and (c)).

1. Methyl 3-[(1H-imidazol-4-yl)methyl]-2-methoxybenzoate.

1.a. Methyl 2-(2-chloro-2-propenyloxy)-benzoate. A suspension of 304 g (2 moles) of methyl 2-hydroxybenzoate, 25 g of potassium iodide, 69 g (0.5 mole) of potassium carbonate, and 69 g (0.625 mole) of 2,3-dichloropropene in 3 liters of dry acetone is heated at reflux temperature for 10 hours. After two and a half hours, five hours and seven and a half hours of reaction time, 69 g of potassium carbonate and 69 g of 2,3-dichloropropene are added each time. Thereafter, the suspension is filtered off and the filtrate is evaporated under reduced pressure. The residue is taken up in ethyl acetate, and the solution is washed successively with a saturated aqueous solution of sodium thiosulfate, with water, and finally with a saturated aqueous solution of sodium chloride. The organic phase is dried over sodium sulfate, and is distilled under reduced pressure. 394 g of methyl 2-(2-chloro-2-propenyloxy)-benzoate are obtained.

Yield: 87% B.P.: 119° C./1.3 mbar.

1.b. Methyl 3-(2-chloro-2-propenyl)-2-hydroxybenzoate. 274.1 g (1.21 mole) of methyl 2-(2-chloro-2-propenyloxy)-benzoate, placed in a 2 liter round-bottomed flask, are carefully degassed with argon. This is then heated as rapidly as possible to 260° C. At this temperature, an exothermic reaction takes place suddenly: the temperature increases to 293° C. by itself and reflux and blackening of the reaction mixture takes place. After cooling to ambient temperature, the product is distilled under reduced pressure. 241.1 g of ethyl 3-(2-chloro-2-propenyl)-2-hydroxybenzoate are obtained.

Yield: 88%. B.P.: 109°–110° C./1.3 mbar.

NMR (CDCl$_3$): delta 3.71(2H,s), 3.95(3H,s), 5.17(1H,m), 5.28(1H,m), 6.90(1H,t), 7.48(1H,dd), 7.85(1H,dd), 11.22(1H,s).

1.c. Methyl 3-(2-chloro-2-propenyl)-2-methoxybenzoate. Without exceeding the temperature of 10° C., 8.81 g (306 mmoles) of sodium hydride are added in portions to a solution of 57.7 g (255 mmoles) of methyl 3-(2-chloro-2-propenyl)-2-hydroxybenzoate in 500 ml of anhydrous dimethylformamide. The mixture is heated to 40° C. for 15 minutes. A solution of 43.45 g (306 mmoles) of methyl iodide in 50 ml of toluene is then added and the temperature of the mixture is maintained at 40° C. for 3 hours. The reaction mixture is carefully poured into 5 liters of water, and is extracted several times with ethyl acetate. The organic phase is concentrated to a volume of 500 ml and is then washed successively with water and with a saturated aqueous solution of sodium chloride. The solution is dried over sodium sulfate and the solvent is evaporated under reduced pressure. The residue is purified by chromatography on silica gel (eluent: 50:50 v/v dichloromethane-hexane). 49.2 g of methyl 3-(2-chloro-2-propenyl)-methoxybenzoate are obtained.

Yield: 60%. B.P.: 107°–110° C./0.5 mbar (oil).

NMR (CDCl$_3$): delta 3.73(2H,s), 3,82(3H,s), 3.92(3H,s), 5.14(1H,m), 5.32(1H,m), 7.15(1H,t), 7.47(1H,dd), 7.81(1H,dd).

1.d. Methyl 3-[(1H-imidazol-4-yl)methyl]-2-methoxybenzoate. A solution of 45.5 g (189 mmoles) of methyl 3-(2-chloro-2-propenyl)-2-methoxybenzoate and of 81.5 g (378 mmoles) of m-chloroperbenzoic acid in 300 ml of dry chloroform is heated to reflux temperature for 150 minutes. It is cooled to 0° C. and the precipitate thus formed is eliminated by filtration. The filtrate is successively washed with a saturated aqueous solution of sodium thiosulfate and with a saturated aqueous solution of sodium bicarbonate. The solution is dried over sodium sulfate and the solvent is evaporated under reduced pressure without exceeding 30° C.

The residue obtained is suspended in 300 ml of anhydrous methanol, and mixed with 111.3 g (1.32 mole) of finely ground sodium bicarbonate. The mixture is heated to reflux temperature. 137.6 g (1.32 mole) of formamidine acetate are added in portions, hourly, to the mixture. After five and a half hours of heating to reflux temperatures, methanol is removed under reduced pressure. The residue is taken up in 500 ml water and extracted with ethyl acetate. The organic phase is dried over sodium sulfate and is evaporated under reduced pressure. The residue is purified by chromatography on silica gel (eluent: 92.3:7:0.7 v/v/v dichloromethane-ethanol-ammonia). 13.8 g of methyl 3-[(1H-imidazol-4-yl)methyl]-2-methoxybenzoate are obtained.

Yield: 30%.

NMR (DMSO): delta 3.73(3H,s), 3.83(3H,s), 3,89(2H,s), 6.78(1H,s), 7.11(1H,t), 7.24 to 7.73(3H,m).

The product obtained is used as such, without further purification, to prepared the corresponding acid (Example 2.B.1.).

The following compounds have been prepared according to the method described in B.1. above.

2. Methyl 2-hydroxy-3-[(1H-imidazol-4-yl)methyl]-benzoate. This compound is prepared from methyl 3-(2-chloro-2-propenyl)-2-hydroxybenzoate with a yield of 35.4%, but of course omitting the methylation with methyl iodide described in B.1.c.

M.P.: 153°–154° C.

The compound is identical with that prepared in Example 1.A.4..

3. Methyl 3-[(1H-imidazol-4-yl)methyl]-2-n-propoxybenzoate.

Yield: 20% (oil).

The crude product is used as such to prepare the corresponding acid (Example 2.B.2.).

C. By Friedel-Crafts reaction (method (d)).

1. Methyl 5-tert-butyl-2-hydroxy-3-[(1H-imidazol-4-yl)methyl]-benzoate hydrochloride. 50 g of 1H-imidazole-4-methanol hydrochloride are reacted with 60 g of methyl 5-tert-butyl-2-hydroxybenzoate in 150 ml of concentrated sulfuric acid at 20° C. for 21 hours. The reaction mixture is then cautiously decomposed on ice.

The solid product is filtered off, purified by chromatography and then converted into its hydrochloride.

1.1 g of methyl 5-tert-butyl-2-hydroxy-3-[(1H-imidazol-4-yl)methyl]-benzoate hydrochloride is obtained.

Yield: 2.8%. M.P.: 185°–186° C.

NMR (DMSO): delta 1.3(9H,s), 3.45(3H,s), 4.1(2H,s), 7.3(1H,s), 7.75(2H,m), 9.0(1H,s), 10.5 to 13,0 (3H).

2. Methyl 2,6-dihydroxy-3-[(1H-imidazol-4-yl)methyl]-benzoate. 95.84 g (0.57 mole) of methyl 2,6-dihydroxybenzoate, 190 ml of formic acid and 51.14 g (0.38 mole) of 1H-imidazole-4-methanol hydrochloride are mixed together. The mixture is heated at reflux temperature and the formic acid-water azeotropic mixture is distilled for 15 minutes. Then, the reflux temperature is maintained for 17 hours. The reaction mixture is poured in water. Excess methyl 2,6-dihydroxybenzote is extracted with toluene, and the aqueous phase is then neutralized to pH 7–8 by the addition of a saturated aqueous solution of sodium hydroxide. It is then extracted with dichloromethane, the organic phases are dried over sodium sulfate and the solvent is evaporated under reduced pressure. The residue is purified by chromatography on silica gel (eluent: 94:6:0.6 v/v/v dichloromethane-methanol-ammonia). 14.8 g of methyl 2,6-dihydroxy-3-[(1H-imidazol-4-yl)methyl]-benzoate are obtained; the product is contaminated by traces of residual solvents. Yield: 13%.

NMR (DMSO): delta 3.72(2H,s), 3.81(3H,s), 6.33(1H,d), 6.86(1H,s), 7.06(1H,d), 7.73(1H,s), 9,5 to 10.2(3H).

In view of its instability, the product thus obtained is used as such, without further purification, to prepare the corresponding benzamide (Example 4.9.).

The following compounds are prepared according to the method described in C.2. above.

3. Methyl 2,6-dihydroxy-3-[1-(1H-imidazol-4-yl)ethyl]-benzoate. This compound is prepared from a α-methyl-1H-imidazole-4-methanol hydrochloride. Reflux temperature is maintained for 19 hours. The residue which is finaly obtained is purified by chromatography on silica gel (eluent: 95:5:0.5 v.v/v dichloromethane-methanol-ammonia).

Yield: 43%.

NMR (CDCl$_3$): delta 1.52(3H,d), 4.0(3H,s), 4.48(1H,q), 6.40(1H,d), 6.79(1H,s), 7.14(1H,d), 7.47(1H,s), 10.0(3H).

The product obtained is used as such, without further purification, to prepare the corresponding benzamide (Example 4.10.).

4. Ethyl 6-hydroxy-3-[(1H-imidazol-4-yl)methyl]-2-methylbenzoate and ethyl 2-hydroxy-3-[(1H-imidazol-4-yl)methyl]-6-methylbenzoate. These two compounds are simultaneously prepared from a mixture of 80.8 g (0.448 mole) of ethyl 2-hydroxy-6-methylbenzoate, 225 ml of formic acid and 51.5 g (0.382 mole) of 1H-imidazole-4-methanol hydrochloride, heated at reflux temperature for 53 hours. The products obtained are separated and purified by chromatography on silica gel (eluent: 94:6:0.5 v/v/v dichloromethane-methanol-ammonia). 7.2 g of ethyl 6-hydroxy-3-[(1H-imidazol-4-yl)methyl]-2-methylbenzoate are obtained.

Yield: 7.2%. M.P.: 42°–45° C.

NMR (CDCl$_3$): delta 1.36(3H,t), 2.34(3H,s), 3.83(2H,s), 4.37(2H,q), 6.52(1H,s), 6.70(1H,d), 7.08(1H,d), 7.45(1H,s), 10.0(2H).

2.8 g of ethyl 2-hydroxy-3-[(1H-imidazol-4-yl)methyl]-6-methylbenzoate are obtained at the same time. Yield: 2.8%. M.P.: 101°–103° C.

NMR (CDCl$_3$): delta 1.40(3H,t), 2.47(3H,s), 3.88(2H,s), 4.39(2H,q), 6.62(1H,d), 6.76(1H,s), 7.12(1H,d), 7.43(1H,s), 10.0(2H).

5. Methyl 2-hydroxy-3-[(1H-imidazol-4-yl)methyl]-4-methylbenzoate bromhydride.

5.a. methyl 5-bromo-2-hydroxy-3-[(1H-imidazol-4-yl)methyl]-4-methylbenzoate. 95.6 g (0.71 mole) of 1H-imidazole-4-methanol hydrochloride are added in portions, at ambient temperature, to a solution of 87 g (0.355 mole) of methyl 5-bromo-2-hydroxy-4-methylbenzoate (T. M. CRESP et al., J. Chem. Soc. Perkin I, (1973), 340) in 900 ml of concentrated sulfuric acid. Stirring is maintained for 234 hours. The reaction mixture is then poured cautiously on ice and the aqueous phase is neutralized to pH 8 by the addition of a saturated aqueous solution of sodium hydroxide. There is extracted with ethyl acetate. The organic layer is evaporated under reduced pressure and the residue is purified by chromatography on 1.4 kg of silica (eluent: 9:1 v/v dichloromethane-methanol). The product obtained is chromatographed a second time on 400 g of silica (eluent: 95:5:0.5 v/v/v dichloromethane-methanol-ammonia). 2.4 g of methyl 5-bromo-2-hydroxy-3-[(1H-imidazol-4-yl)methyl]-4-methylbenzoate are obtained, which are sufficiently pure to be used as such in the following step.

NMR (DMSO): delta 2.43(3H,s), 3.90(3H,s), 3.96(2H,s), 6.62(1H,s), 7.51(1H,s), 7.87(1H,s).

5.b. methyl 2-hydroxy-3-[(1H-imidazol-4-yl)methyl]-4-methylbenzoate bromhydride. 2.38 g (7.2 mmoles) of methyl 5-bromo-2-hydroxy-3-[(1H-imidazol-4-yl)methyl]-4-methylbenzoate dissolved in 70 ml of methanol, are subjected to hydrogenolysis at ambient temperature, in the presence of 0.7 g of 10% palladium on carbon, under a hydrogen pressure of 4.2 bars. The catalyst is filtered off and the solvent is evaporated under reduced pressure. 1.83 g of methyl 2-hydroxy-3-[(1H-imidazol-4-yl)methyl]-4-methylbenzoate bromhydride is obtained. Yield: 76%.

NMR (DMSO): delta 2.34(3H,s), 3.91(3H,s), 4.02(2H,s), 6.87(1H,s), 7.13(1H,s), 7.68(1H,d), 8.86(1H,s).

The product thus obtained is used as such, without further purification, to prepare the corresponding benzamide (Example 4.14.).

EXAMPLE 2. PREPARATION OF THE STARTING 1-(1H-IMIDAZOL-4-YL)ALKYL-BENZOIC ACIDS OF FORMULA IV.

A. By oxidation of the corresponding 1-(1H-imidazol-4-yl)alkyl-benzenemethanols.

1. 2-hydroxy-3-[(1H-imidazol-4-yl)methyl]-benzoic acid (hydrochloride). 1 g of 2-hydroxy-3-[(1H-imidazol-4-yl)methyl]-benzenemethanol (prepared by the method described in Example 6.1 of the abovementioned U.S. patent application Ser. No. 116,325) is heated at 180° C. for two hours and a half and with thorough stirring, in the presence of 7.5 g of potassium hydroxide. The reaction mixture is then cooled and dissolved in 10 ml of water. The aqueous solution is acidified to pH 3–4 by addition of concentrated hydrochloric acid. The precipitate which separates is filtered off and dried, and is then extracted with boiling isopropyl alcohol. The isopropyl alcohol is then eliminated under reduced pressure, and the crystalline residue obtained is recrystallized in 5 ml of an 1N aqueous solution of hydrochloric acid. 0.74 g of 2-hydroxy-3-[(1H-imidazol-4-yl)methyl]-benzoic acid hydrochloride is obtained.
Yield: 58% M.P.: 257° C. (decomp.).
NMR (DMSO): delta 4.08(2H,s), 6.09(1H,t), 7.37(1H,d), 7.52(1H,dd), 7.79(1H,dd), 9.05(1H,d).

| Analysis for $C_{11}H_{10}N_2O_3 \cdot HCl$ in % | | | |
|---|---|---|---|
| calc.: | C 51.87 | H 4.32 | N 11.0 |
| found: | 51.68 | 4.03 | 10.61 |

This compound is used as starting material in Example 1.A.4. The following compound has been prepared in the same way.

2. 2-hydroxy-3-[1-(1H-imidazol-4-yl)ethyl]-benzoic acid. This compound, used as the starting material in Example 1.A.2., is prepared from 2-hydroxy-3-[1-(1H-imidazol-4-yl)ethyl]-benzenemethanol with a yield of 50%.
The free acid is obtained by neutralization of the hydrochloride and recrystallization from water.
M.P.: 278°–280° C.

| Analysis for $C_{12}H_{12}N_2O_3$ in % | | | |
|---|---|---|---|
| calc.: | C 62.06 | H 5.17 | N 12.07 |
| found: | 62.05 | 5.37 | 11.72 |

The 2-hydroxy-3-[1-(1H-imidazol-4-yl)ethyl]-benzenemethanol used as starting material is prepared using the method described in Example 6.5. of the above-mentioned U.S. patent application Ser. No. 116,325.

3. 2-hydroxy-3-[1-(1H-imidazol-4-yl)pentyl]-benzoic acid (hydrochloride). 3.86 g (14.8 mmoles) of 2-hydroxy-3-[1-(1H-imidazol-4-yl)pentyl]-benzenemethanol (prepared according to the method described in Example 6.6. of the above-mentioned U.S. patent application Ser. No. 116,325) are heated at 170° C. for 5 hours, in the presence of 22 g of potassium hydroxide. Then the reaction medium is cooled and dissolved in 100 ml of water. The insoluble material is filtered off and the filtrate is acidified to pH 10 by the addition of concentrated hydrochloric acid. The salts which separate are eliminated by filtration and the filtrate is finally acidified to pH 1. The 2-hydroxy-3-[1-(1H-imidazol-4-yl)pentyl]-benzoic acid hydrochloride separates. It is recrystallized from 100 ml of isopropyl alcohol. 1.44 g of the product is obtained.
M.P.: 239°–251° C.
NMR (DMSO): delta 0.83(3H,t), 1.17 to 1,32(4H,m), 1.94 to 2.07(2H,m), 4.43(1H,t), 6.79(1H,t), 7.33(1H,d), 7.47(1H,s), 7.69(1H,d), 8.84(1H,s).
This compound is used as starting material in Example 1.A.3.

B. By hydrolysis of the corresponding esters prepared via the Claisen transformation.

1. 3-[(1H-imidazol-4-yl)methyl]-2-methoxybenzoic acid. 4.3 g (17.5 mmoles) of methyl 3-[(1H-imidazol-4-yl)methyl]-2-methoxybenzoate (prepared in Example 1.B.1.) dissolved in 20 ml of methanol and 21 ml of a 1N aqueous solution of sodium hydroxide are heated under reflux for 3 hours. The methanol is evaporated under reduced pressure and the aqueous solution is acidified to pH 5 by the addition of 21 ml of a 1N aqueous solution of hydrochloric acid. The precipitate formed is filtered off, the filtrate is concentrated to half of its volume and the new precipitate which appears is also filtered off. The two crops are washed with hexane and dried under reduced pressure. 3.16 g of practically pure 3-[(1H-imidazol-4-yl)methyl]-2-methoxybenzoic acid are obtained. Yield: 78%.
NMR (DMSO+CF$_3$COOH): delta 3.78(3H,s), 4.07(2H,s), 6.96 to 7.82(4H,m), 8.91(1H,s).
The product obtained is used as such to prepare the corresponding benzamide (Example 5.1.).
The following compound has been prepared in the same way.

2. 3-[(1H-imidazol-4-yl)methyl]-2-n-propoxybenzoic acid. This is obtained from methyl 3-[(1H-imidazol-4-yl)methyl]-2-n-propoxybenzoate (prepared in Example 1.B.3.). The product obtained is used as such to prepare the corresponding benzamide (Example 5.2.).

C. By hydrolysis of the esters obtained by the Friedel-Crafts reaction. 2-hydroxy-3-[(1H-imidazol-4-yl)methyl]-benzoic acid and 2-hydroxy-5-[(1H-imidazol-4-yl)methyl]-benzoic acid (hydrochloride).
181 g (1.35 mole) of 1H-imidazole-4-methanol hydrochloride are added in portions to a mixture of 156 ml (1.2 mole) of methyl 2-hydroxybenzoate and 675 g of polyphosphoric acid heated to 80° C. The reaction mixture is maintained with good stirring at this temperature for 288 hours. The mixture is then decomposed on ice, and extracted twice with toluene. The aqueous phase is alkalinized to pH 9.5 by the addition of 790 ml of a saturated aqueous solution of sodium hydroxide. The mineral salts which precipitate are removed by filtration and washed with methanol. The methanolic washing solution is added to the aqueous phase and the resulting mixture is concentrated with partial elimination of the methanol. The solution is then alkalinized to pH 10.3 by addition of a 10N aqueous solution of sodium hydroxide, and is heated at 100° C. for one hour and a half so as to saponify the esters. The aqueous solution is neutralized to pH 7.5 by addition of 10N hydrochloric acid, filtered on Norit (activated carbon) and the filtrate is evaporated under reduced pressure. The residue is taken up three times in succession in a toluene-ethanol mixture and dried by azeotropic distillation. It is then partially dissolved in hot methanol and the insoluble mineral salts are removed by filtration. The filtrate is evaporated under reduced pressure, the residue is redissolved in a minimum of water, and purification is then carried out by passing through a column of Amberlite IR93 (height of the column: 60 cm; diameter: 8 cm; equivalence: 2.64 mole). Excess 1H-imidazole-4-methanol, together with its polymers, are eluted with water (the pH of the eluate varies from 11.2 to 7.3). The elution is then continued with a 4% aqueous solution of hydrochloric acid.

The acid eluate (9 liters) is adjusted to pH 7.7 by addition of a saturated agueous solution of sodium hydroxide and is then evaporated under reduced pressure. The residue thus obtained is once again dried by azeotropic distillation with a toluene-ethanol mixture, and is then taken up in 1.6 liter of acetonitrile. It is then filtered. The residue on the filter (129 g) is chromatographed on silica (800 g, 15 μm) after having been previously deposited on 300 g of silica (0.2 to 0.5 mm) (eluent: 75:25 v/v ethyl acetate-ethanol). 5.99 g of 2-hydroxy-3-[(1H-imidazol-4-yl)methyl]-benzoic acid is thus obtained. M.P.: 245°–252° C. (water).

| Analysis for $C_{11}H_{10}N_2O_3$ in % | | | |
|---|---|---|---|
| calc.: | C 60.56 | H 4.59 | N 12.04 |
| found: | 60.32 | 4.69 | 12.41 |

At the same time, 31 g of 2-hydroxy-5-[(1H-imidazol-4-yl)methyl]-benzoic acid are obtained. Its hydrochloride, used as starting material in Example 1.A.1., melts at 254°–258° C. (methanol-diethyl ether).

| Analysis for $C_{11}H_{10}N_2O_3 \cdot HCl$ in %: | | | | |
|---|---|---|---|---|
| calc.: | C 51.87 | H 4.32 | N 11.0 | Cl⁻ 13.40 |
| found: | 51.65 | 4.24 | 10.45 | 13.73 |

EXAMPLE 3. PREPARATION OF THE STARTING 2-HYDROXY-3-[1-(1H-IMIDAZOL-4-YL)ALKYL]-BENZONITRILES OF FORMULA V.

1. 2-hydroxy-3-[(1H-imidazol-4-yl)methyl]-benzonitrile.

1.a. Ethyl 4-benzyloxy-2-[(1H-imidazol-4-yl)methyl]-3-oxo-butanoate. 182 g (0.77 mole) of ethyl 4-benzyloxy-3-oxo-butanoate are added at once, at a temperature of 10° C., to a solution of 16.9 g (0.735 mole) of sodium in 590 ml of absolute ethanol. The mixture is stirred for 45 minutes at ambient temperature and then cooled to −45° C. A solution of 53.6 g (0.35 mole) of 4-chloromethyl-1H-imidazole hydrochloride in 300 ml of absolute ethanol is added thereto, at once. The mixture is allowed to return to ambient temperature and is stirred for 1 hour. Subsequently, the suspension is evaporated to dryness. The residue is taken up in 35 ml of a solution of concentrated hydrochloric acid in 900 ml of water, and is then extracted several times with diethyl ether. The aqueous phase is neutralized with a solution of 18 g of sodium hydroxide in 200 ml of water and is then extracted several times with ethyl acetate. The organic phases are washed successively with water and with a saturated aqueous solution of sodium chloride. It is dried over sodium sulfate and evaporated under reduced pressure. 107 g of practically pure ethyl 4-benzyloxy-2-[(1H-imidazol-4-yl)methyl]-3-oxo butanoate are obtained. Yield: 97%.

NMR (DMSO): delta 1.11(3H,t), 2.98(2H,m), 4.05(2H,q), 4.08(1H,m), 4.25(2H,dd), 4.47(2H,s), 6.75(1H,s), 7.25 to 7.39(5H,m), 7.47(1H,d).

1.b. Ethyl 4-benzyloxy-3-hydroxy-2-[(1H-imidazol-4-yl)methyl]-butanoate. An ice-cold solution of 6.03 g (0.16 mole) of sodium borohydride in 25 ml of water, is added at once to a solution of 101.2 g (0.32 mole) of ethyl 4-benzyloxy-2-[(1H-imidazol-4-yl)methyl]-3-oxo-butanoate in 600 ml of ethanol previously cooled to −20° C. The mixture is allowed to return to ambient temperature and is stirred for one hour. Subsequently, 25 ml of acetone are added. The solution is evaporated to dryness and the residue is taken up in 500 ml of water. It is extracted several times with ethyl acetate. The organic phases are washed with water and with a saturated aqueous solution of sodium chloride. They are dried over sodium sulfate and the solvent is evaporated under reduced pressure. The residue is purified by chromatography on silica gel (eluent: 93:5:6:0.5 v/v/v dichloromethane-methanol-ammonia).

95.8 g of ethyl 4-benzyloxy-3-hydroxy-2-[(1H-imidazol-4-yl)methyl]-butanoate are obtained (mixture of diastereoisomers). Yield: 94%.

NMR (CDCl₃): delta 1.15 and 1.16(3H,2t), 2.90 to 3.05(3H,m), 3.51 to 3.58(2H,m), 3.96 to 4.11(3H,2q+1m), 4.51 and 4.53(2H,2s), 6.73 and 6.75(1H,2s), 7.25 to 7.36(5H,m).

1.c. 4-hydroxy-3-[-(1H-imidazol-4-yl)methyl]-dihydro-2(3H)-furanone hydrochloride. 93.9 g (0.295 mole) of ethyl 4-benzyloxy-3-hydroxy-2-[(1H-imidazol-4-yl)methyl]-butanoate dissolved in 500 ml of absolute ethanol and 65 ml of a 6.8N ethanolic solution of hydrochloric acid, are subjected to hydrogenolysis in the presence of 5 g of 10% palladium on carbon under a hydrogen pressure of 3.5 bars. The catalyst is then filtered off and the solvent is eliminated at 65° C. under reduced pressure. 67.1 g of 4-hydroxy-3-[(1H-imidazol-4-yl)methyl]-dihydro-2(3H)-furanone hydrochloride are obtained (mixture of diastereoisomers). Practically quantitative yield. The product obtained is used as such in the following step.

1.d. 3-[(1H-imidazol-4-yl)methyl]-2(5H)-furanone. 67.1 g (0.295 mole) of 4-hydroxy-3-[(1H-imidazol-4-yl)methyl]-dihydro- 2(3H)-furanone hydrochloride are heated at 160° C. for 75 minutes under a pressure of 0.0013 mbar, the cooled and taken up in 125 ml of absolute ethanol. It is neutralized by addition of 70 ml of a 5N ethanolic solution of ammonia. The suspension is filtered off and the solvent is removed under reduced pressure. The residue is purified by chromatography on silica gel (eluent: 91.5:8:0.5 v/v/v dichloromethane-methanol-ammonia). After recrystallization from acetonitrile, 27.5 g of 3-[(1H-imidazol-4-yl)methyl]-2(5H)-furanone are obtained. Yield: 53% (calculated on steps 1.c. and 1.d. together). M.P.: 123° C.

NMR (CDCl₃): delta 3.63(2H,q), 4.79(2H,q), 6.90(1H,d), 7.25(1H,quintet), 7.52(1H,d).

1.e. 2-hydroxy-3-[(1H-imidazol-4-yl)methyl]-benzonitrile. 63 ml (0.45 mole) of anhydrous triethylamine and 57 ml (0.45 mole) of trimethylchlorosilane are successively added to a suspension of 24.6 g (0.15 mole) of 3-[(1H-imidazol-4-yl)methyl]-2(5H)-furanone in 225 ml of anhydrous acrylonitrile. The mixture is heated under reflux (72° to 74° C.) for 4 hours. It is then evaporated under reduced pressure. The residue is treated at once with 75 ml of concentrated hydrobromic acid and is maintained at 80° C. for 2 minutes. The solution is then poured on ice, diluted by addition of 300 ml of ethyl acetate and 300 ml of water and then neutralized with solid sodium bicarbonate. It is filtered on Celite (diatomaceous earth) and the filtrate is extracted several times with ethyl acetate. The organic phases are washed with water and with a saturated aqueous solution of sodium chloride, then dried over sodium sulfate and evaporated under reduced pressure. The residue obtained is triturated in diethyl ether. 22.8 g of 2-hydroxy-3-[(1H-imidazol-4-yl)methyl]-benzonitrile are obtained. Yield: 76%.

NMR (DMSO): delta 3.90(2H,s), 6.88(1H,t), 7.06(1H,s), 7.41(1H,dd), 7.47(1H,dd), 7.99(1H,d). Its hydrochloride melts at 245° C.

2. 2-hydroxy-3-[1-(1H-imidazol-4-yl)ethyl]-benzonitrile.

2.a. Ethyl 4-benzyloxy-2-[1-(1H-imidazol-4-yl)ethyl]-3-oxo-butanoate. This compound is prepared as described in 1.a. above, starting from ethyl 4-benzyloxy-3-oxo-butanoate and from 4-(1-chloroethyl)-1H-imidazole. Yield: 68% (mixture of diastereoisomers).

NMR (CDCl$_3$): delta 1.10 and 1.22(3H,2t), 1.33 and 1.36(3H,2d), 3.60 to 3.72(1H,m), 3.93 to 4.20(3H,m), 4.47 and 4.55(1H,2s), 6.70 and 6.74(1H,2s), 7.26 to 7.35(5H,m), 7.41 and 7.45(1H,s+d).

2.b. Ethyl 4-benzyloxy-3-hydroxy-2-[1-(1H-imidazol-4-yl)ethyl]-butanoate. This compound is prepared as described in 1.b. above, by reduction of ethyl 4-benzyloxy-2-[1-(1H-imidazaol-4-yl)ethyl]-3-oxo-butanoate.

Yield: 91% (mixture of diastereoisomers).

Mass spectrum: 332 (M+), 314, 287, 211, 181, 135, 95, 91.

2.c. 4-hydroxy-3-[1-(1H-imidazol-4-yl)ethyl]-dihydro-2(3H)-furanone hydrochloride. This compound is prepared as described in 1.c. above, by hydrogenolysis of ethyl 4-benzyloxy-3-hydroxy-2-[1-(1H-imidazol-4-yl)ethyl]-butanoate. Practically quantitative yield. A mixture of diastereoisomers is obtained and is used as such in the following step.

2.d. 3-[1-(1H-imidazol-4-yl)ethyl]-2(5H)-furanone. 75.1 g (0.32 mole) of 4-hydroxy-3-[1-(1H-imidazol-4-yl)ethyl]-dihydro-2(3H)-furanone hydrochloride in 30 ml of ethylene glycol are heated at 170° C. for one hour under a pressure of 13.3 mbars. The solvent is then removed under a pressure of 0.0013 mbar. The residue is taken up in 300 ml of absolute ethanol and is neutralized by addition of 63.2 ml of a 5N ethanolic solution of ammonia. The suspension is filtered off and the solvent is evaporated under reduced pressure. The residue is purified by chromatography on silica gel (eluent: 91.5:8:0.5 v/v/v dichloromethane-methanol-ammonia). After recrystallization from acetonitrile, 41.9 g of 3-[1-(1H-imidazol-4-yl)ethyl]-2(5H)-furanone are obtained. Yield: 74% (calculated on steps 2.c. and 2.d. together). M.P.: 127°–129° C.

NMR (DMSO): delta 1.40(3H,d), 3.72(1H,q), 4,84(2H,t), 6.80(1H,t), 7.35(1H,q), 7.51(1H,s).

2.e. 2-hydroxy-3-[1-(1H-imidazol-4-yl)ethyl]-benzonitrile. 56 ml (0.4 mole) of anhydrous triethylamine and 50.7 ml (0.4 mole) of trimethylchlorosilane are successively added to a suspension of 17.8 g (0.1 mole) of 3-[1-(1H-imidazol-4-yl)ethyl]-2(5H)-furanone in 150 ml of anhydrous acrylonitrile. The mixture is heated under reflux for 3 hours and a half. The reaction mixture is then evaporated under reduced pressured. The residue is treated at once with 50 ml of concentrated hydrochloric acid and is maintained at 80° C. for 2 minutes. The solution is then poured on ice, neutralized with a saturated aqueous solution of sodium bicarbonate and extracted several times with ethyl acetate. The organic phases are washed with water and with a saturated aqueous solution of sodium chloride, then dried over sodium sulfate and evaporated under reduced pressure. The residue is purified by chromatography on silica gel (eluent: 93.5:6:0.5 v/v/v dichloromethane-methanol-ammonia). 17.6 g of practically pure 2-hydroxy-3-[1-(1H-imidazol-4-yl)ethyl]-benzonitrile are obtained. Yield: 83%. M.P.: 172° C.

NMR (DMSO): delta 1.52(3H,d), 4.21(1H,q), 6.86(1H,t), 7.02(1H,s), 7.41(1H,dd), 7.44(1H,dd), 7.85(1H,s).

EXAMPLE 4. PREPARATION OF THE 1-(1H-IMIDAZOL-4-YL)ALKYL-BENZAMIDES OF FORMULA I BY REACTION OF THE ESTERS OF FORMULA II WITH A NITROGEN COMPOUND OF FORMULA III.

1. 2-hydroxy-3-[1-(1H-imidazol-4-yl)methyl]-benzamide hydrochloride. A stream of ammonia gas, dried on potassium hydroxide, is passed into a solution of 18.1 g (78 mmoles) of methyl 2-hydroxy-3-[(1H-imidazol-4-yl)methyl]-benzoate (prepared in Example 1.B.2. and in Example 1.A.4.) in 400 ml of anhydrous methanol, for one night. It is then heated under reflux for 2 hours. The reaction mixture is then evaporated under reduced pressure, and the residue is purified by chromatography on silica gel (eluent: 89.5:10:0.5 v/v/v dichloromethane-methanol-ammonia).

16.6 g of 2-hydroxy-3-[(1H-imidazol-4-yl)methyl]-benzamide are obtained.

Yield: 98%. M.P.: 197.6° C.

| Analysis for $C_{11}H_{11}N_3O_2$ in %: | | |
| --- | --- | --- |
| calc.: C 60.83 | H 5.07 | N 19.35 |
| found: 60.91 | 5.06 | 19.32 |

The amide, treated in ethanol with 1.2 equivalent of hydrochloric acid, gives a hydrochloride with a yield of 73%.

M.P.: 287.8° C.

| Analysis for $C_{11}H_{11}N_3O_2 \cdot HCl$ in %: | | | |
| --- | --- | --- | --- |
| calc.: C 52.07 | H 4.73 | N 16.57 | Cl$^-$ 14.00 |
| found: 52.04 | 4.76 | 16.54 | 13.94 |

2. 2-hydroxy-5-[(1H-imidazol-4-yl)methyl]-benzamide. This compound is prepared as described in 1. above, starting from ethyl 2-hydroxy-5-[(1H-imidazol-4-yl)methyl]-benzoate hydrochloride (prepared in Example 1.A.1.). The reaction mixture is stirred for three days at ambient temperature. The product of the reaction is purified by chromatography on silica gel (eluent: 85:15 v/v dichloromethane-methanol). M.P.: 180°–185° C. (isopropyl alcohol).

| Analysis for $C_{11}H_{11}N_3O_2$ in % | | | |
|---|---|---|---|
| calc.: | C 60.83 | H 5.07 | N 19.35 |
| found: | 60.71 | 5.25 | 19.01 |

3. 2-hydroxy-3-[(1H-imidazol-4-yl)methyl]-N-methyl-benzamide hydrochloride. 6.96 g (30 mmoles) of methyl 2-hydroxy-3-[(1H-imidazol-4-yl)methyl]-benzoate (prepared in Example 1.B.2.) and 60 ml of methylamine dissolved in 350 ml of ethanol, are heated in an autoclave at 75° C. for 3 hours. The mixture is evaporated under reduced pressure. The residue is taken up in water and extracted three times with ethyl acetate. The organic phase is dried over sodium sulfate and the solvent is evaporated under reduced pressure. The residue is purified by chromatography on silica gel (eluent: 91.5:8.0:0.5 v/v/v dichloromethane-methanol-ammonia). After the solvents have been evaporated, the product thus obtained is crystallized from ethyl acetate. 4.95 g of 2-hydroxy-3-[(1H-imidazol-4-yl)methyl]-N-methlbenzamide is obtained. Yield: 71%.

The amide, treated in a mixture of ethanol and ether with 1.2 equivalent of hydrochloric acid, yields 4.7 g of hydrochloride. Yield: 59%. M.P.: 233.9° C.

| Analysis for $C_{12}H_{13}N_3O_2 \cdot HCl$ in % | | | |
|---|---|---|---|
| calc.: | C 53.83 | H 5.23 | N 15.70 |
| found: | 53.74 | 5.17 | 15.55 |

4. 2-hydroxy-3-[(1H-imidazol-4-yl)methyl]-benzohydrazide. A mixture of 10 g (43.1 mmoles) of methyl 2-hydroxy-3-[(1H-imidazol-4-yl)methyl]-benzoate (prepared in Example 1.B.2.) and 4.31 g (86.2 mmoles) of hydrazine hydrate, dissolved in 100 ml of methanol, is heated under reflux for 13 hours. 2.15 g (43.1 mmoles) of hydrazine hydrate are added again and the heating under reflux is maintained for another 24 hours. The mixture is then evaporated under reduced pressure. The residue is taken up in 100 ml of water (pH=8). The solution is saturated with sodium chloride and extracted with ethyl acetate. The organic phase is dried over sodium sulfate, and the solvent is evaporated under reduced pressure. The residue is crystallized from ethanol. 6.1 g of 2-hydroxy-3-[(1H-imidazol-4-yl)methyl]-benzohydrazide, recrystallizable from methanol, are obtained. Yield: 61%. M.P.: 189.7° C.

| Analysis for $C_{11}H_{12}N_4O_2$ in % | | | |
|---|---|---|---|
| calc.: | C 56.88 | H 5.21 | N 24.13 |
| found: | 56.91 | 5.24 | 24.00 |

5. 2-hydroxy-3-[1-(1H-imidazol-4-yl)ethyl]-benzamide hydrochloride. A solution of 2 g of ethyl 2-hydroxy-3-[1-(1H-imidazol-4-yl)ethyl]-benzoate (prepared in Example 1.A.2.) in 50 ml of methanol, through which a stream of gaseous ammonia is passed, is stirred for 90 hours at ambient temperature and in the presence of a catalytic amount of 20 mg of sodium methoxide. The methanol is then evaporated, and the residue is purified by chromatography on silica gel (eluent: 8.5:1:0.5 v/v/v dichloromethane-methanol-ammonia). The product obtained is converted into the hydrochloride in a solution of hydrochloric acid in ethanol in the presence of diethyl ether. 1.2 g of 2-hydroxy-3-[1-(1H-imidazol-4-yl)ethyl]-benzamide hydrochloride is obtained. Yield: 68%. M.P.: 240°–243° C.

| Analysis for $C_{12}H_{13}N_3O_2 \cdot HCl$ in % | | | | |
|---|---|---|---|---|
| calc.: | C 53.83 | H 4.86 | N 15.70 | Cl⁻ 13.27 |
| found: | 54.0 | 4.88 | 15.73 | 13.17 |

The amide obtained after purification by chromatography on silica gel is resolved into its two enantiomers by chromatography on a chiral phase of α-glycoprotein (eluent: 1:99 v/v isopropyl alcohol-phosphate buffer 0.02M, pH 7). Each of the enantiomers of the amide is then converted into the corresponding hydrochloride according to the method indicated above. There are thus obtained in almost equal amounts:

(a) hydrated (+)-2-hydroxy-3-[1-(1H-imidazol-4-yl)ethyl]-benzamide hydrochloride. M.P.: 107.8° C. (water).
$[\alpha]_D^{25} = +82.04°$ (c=1, methanol).
NMR (DMSO): delta 1.57(3H,d), 3.30(5H,m), 4.56(1H,q), 6.83(1H,t), 7.23(1H,dd), 7.40(1H,s), 7.82(1H,dd), 7.92(1H,m), 8.51(1H,m), 8.98(1H,d), 13.5 to 14.5(2H,m).

(b) hydrated (−)-2-hydroxy-3-[1-(1H-imidazol-4-yl)ethyl]-benzamide hydrochloride. M.P.: 107.4° C. (water).
$[\alpha]_D^{25} = -79.13°$ (c=1, methanol). The NMR spectrum is identical with that of the other isomer.

6. 2-hydroxy-5-[(1H-imidazol-4-yl)methyl]-N-methyl-benzamide. This compound is prepared according to the method described in 3. above, starting from ethyl 2-hydroxy-5-[(1H-imidazol-4-yl)methyl]-benzoate hydrochloride (prepared in Example 1.A.1.) and from methylamine. The base is previously liberated from the hydrochloride by a slight excess (1.2 equivalent) of sodium methoxide. The product obtained after evaporation of the solvent is purified by chromatography on silica gel (eluent: 97.5:12:0.5 v/v/v dichloromethane-ethanol-ammonia). Yield: 67% (after recrystallization from ethanol). M.P.: 219.5° C.

| Analysis for $C_{12}H_{13}N_3O_2$ in %: | | | |
|---|---|---|---|
| calc.: | C 62.32 | H 5.67 | N 18.17 |
| found: | 62.23 | 5.65 | 18.06 |

NMR (DMSO): delta 2.80(3H,d), 3.27(1H,s), 3.76(2H,s), 6.67(1H,s), 6.80(1H,d) 7.23(1H,dd), 7.49(1H,s), 7.87(1H,d), 8.80(1H,s), 11.8(1H,s).

7. 1-[2-hydroxy-5-[(1H-imidazol-4-yl)methyl]benzoyl]-pyrrolidine. A solution of 300 mg of ethyl 2-hydroxy-5-(1H-imidazol-4-yl)methyl]-benzoate hydrochloride (prepared in Example 1.A.1.) in 5 ml of pyrrolidine, is heated under reflux for 30 minutes. Excess amine is removed under reduced pressure and the residue is purified by chromatography on silica (eluent: 88.5:11:0.5 v/v/v dichloromethane-ethanal-ammonia). 120 mg of 1-[2-hydroxy-5-[(1H-imidazol-4-yl)methyl]benzoyl]-pyrrolidine are obtained. M.P.: 96°-98° C. Yield: 36%.

NMR (DMSO): delta 1.81(4H,s), 3.35(4H,s), 3.74(2H,s), 6.70(1H,s), 6.78(1H,d), 7.04(1H,d), 7.08(1H,dd), 7.50(1H,s), 9.85(1H,s), 11.8(1H,s).

8. 5-tert-butyl-2-hydroxy-3-[(1H-imidazol-4-yl)methyl]-benzamide. This compound is prepared as indicated in 2. above, starting from methyl 5-tert-butyl-2-hydroxy-3-[(1H-imidazol-4-yl)methyl]-benzoate hydrochloride (prepared in Example 1.C.1.). Yield: 22.7%. M.P.: 209°-211° C. (tetrahydrofuran).

| Analysis for $C_{15}H_{19}N_3O_2$ in % | | | |
|---|---|---|---|
| calc.: | C 65.91 | H 7.00 | N 15.37 |
| found: | 65.42 | 7.06 | 15.14 |

9. 2,6-dihydroxy-3-[(1H-imidazol-4-yl)methyl]-benzamide hydrochloride. This compound is prepared as described in 1. above, starting from methyl 2,6-dihydroxy-3-[(1H-imidazol-4-yl)methyl]-benzoate (prepared in Example 1.C.2.). A stream of gaseous ammonia is bubbled for 3 hours through the solution which is maintained at ambient temperature. Then it is evaporated. The residue is recrystallized from dioxane. Yield: 81%. The amide, treated in ethanol with 1.2 equivalent of hydrochloric acid, is converted into the hydrochloride with a yield of 73%. M.P.: 290.3° C. (decomp.).

| Analysis for $C_{11}H_{11}N_3O_3.HCl$ in % | | | |
|---|---|---|---|
| calc.: | C 48.99 | H 4.49 | N 15.58 | Cl− 13.15 |
| found: | 48.79 | 4.43 | 15.44 | 13.16 |

10. 2,6-dihydroxy-3-[1-(1H-imidazol-4-yl)ethyl]-benzamide hydrochloride. This compound is prepared as described in 9. above, starting from methyl 2,6-dihydroxy-3-[1-(1H-imidazol-4-yl)ethyl]-benzoate (prepared in Example 1.C.3.). The residue is recrystallized from toluene. Yield: 85%. The amide, treated in a mixture of ethanol and diethyl ether with 1.1 equivalent of hydrochloric acid, is converted into the hydrochloride.

Yield: 77% (after recrystallization from water). M.P.: 288.8° C. (decomp.).

| Analysis for $C_{12}H_{13}N_3O_3.HCl$ in %: | | | |
|---|---|---|---|
| calc. | C 50.80 | H 4.97 | N 14.81 | Cl− 12.50 |
| found | 50.68 | 4.92 | 14.67 | 12.09 |

11. 6-hydroxy-3-[(1H-imidazol-4-yl)methyl]-2-methylbenzamide hydrochloride. A solution of 6.1 g (23.4 mmoles) of ethyl 6-hydroxy-3-[(1H-imidazol-4-yl)methyl]-2-methylbenzoate (prepared in Example 1.C.4.) in 400 ml of liquid ammonia, is heated in an autoclave at 60° C. for 72 hours. The mixture is then evaporated under reduced pressure and the residue is purified by chromatography on silica gel (eluent: 80:20:0.5 v/v/v ethyl acetate-ethanol-ammonia). 3.3 g of 6-hydroxy-3-[(1H-imidazol-4-yl)methyl]-2-methylbenzamide are obtained. Yield: 61%. The amide, treated in ethanol with 1.1 equivalent of hydrochloric acid, is converted into the hydrochloride. Yield: 66% (after recrystallization from water). M.P.: 262.8° C.

| Analysis for $C_{12}H_{13}N_3O_2.HCl$ in %: | | | |
|---|---|---|---|
| calc. | C 53.84 | H 5.27 | N 15.70 | Cl− 13.24 |
| found | 54.22 | 5.29 | 15.74 | 13.12 |

12. 2-hydroxy-3-[(1H-imidazol-4-yl)methyl]-6-methylbenzamide hydrochloride. This compound is prepared as described in 11. above, starting from 2 g (7.68 mmoles) of ethyl 2-hydroxy-3-[(1H-imidazol-4-yl)methyl]-6-methylbenzoate (prepared in Example 1.C.4.) and from 12 ml of liquid ammonia. The mixture is heated at 60° C. for 24 hours and is then evaporated under reduced pressure. The crude amide is treated, without purification, with 1.1 equivalent of hydrochloric acid in a mixture of ethanol and diethyl ether. The hydrochloride recrystallizes from tetrahydrofuran. Yield: 49%, M.P.: 164.8° C. (mixture of amorphous and crystalline products).

| Analysis for $C_{12}H_{13}N_3O_2.HCl$ in %: | | | |
|---|---|---|---|
| calc. | C 53.84 | H 5.27 | N 15.70 | Cl− 13.24 |
| found | 52.55 | 5.30 | 15.65 | 13.92 |

13. N,2-dihydroxy-3-[(1H-imidazol-4-yl)methyl]-benzamide hydrochloride monohydrate. A solution of 5 g (125 mmoles) of sodium hydroxide in 15 ml of water is added dropwise to a mixture of 4.1 g (25 mmoles) of hydroxylamine sulfate and 25 g of ground ice. When the temperature is returned to 0° C., 0.5 g of solid sodium sulfite is added, followed by 6.15 g (25 mmoles) of ethyl 2-hydroxy-3-[(1H-imidazol-4-yl)methyl]-benzoate. After solution is complete, the reaction mixture is neutralized with 20.8 ml of a 6N aqueous solution of hydrochloric acid. The white precipitate which separates is filtered off, washed with water and purified by chromatography on silica gel (eluent: 76:20:2:2 v/v/v dichloromethane-methanol-acetic acid-water). The acetate obtained after evaporation of the solvents is taken up in 30 ml of water to which are added 5 ml of concentrated hydrochloric acid. The N,2-dihydroxy-3-[(1H-imidazol-4-yl)methyl]-benzamide hydrochloride precipitates in the form of the monohydrate. 4.8 g of pure product are obtained. Yield: 55%. M.P.: 240° C. (decomp.).

| Analysis for $C_{11}H_{11}N_3O_3.HCl.H_2O$ in %: | | | |
|---|---|---|---|
| calc. | C 45.92 | H 4.90 | N 14.61 | Cl− 12.32 |
| found | 46.33 | 4.63 | 14.69 | 12.57 |

The ethyl 2-hydroxy-3-[(1H-imidazol-4-yl)methyl]-benzoate used as starting material is prepared according to the method described in Example 7 of the aforementioned U.S. patent application Ser. No. 116,325.

14. 2-hydroxy-3-[(1H-imidazol-4-yl)methyl]-4-methylbenzamide. This compound is prepared as indicated in 2. above, starting from methyl 2-hydroxy-3-[(1H-imidazol-4-yl)methyl]-4-methylbenzoate hydrobromide (prepared in Example 1.C.5.). The reaction product is purified by chromatography on silica gel (eluent: 95:5:0.5 v/v/v dichloromethane-methanol-ammonia). Yield: 44%. M.P.: 172°-178° C. (diethyl ether).

| Analysis for $C_{12}H_{13}N_3O_2$ in %: | | | |
|---|---|---|---|
| calc. | C 62.33 | H 5.62 | N 18.18 |
| found | 62.42 | 5.61 | 18.08 |

15. 2-hydroxy-3-[1-(1H-imidazol-4-yl)pentyl]-benzamide hydrochloride. This compound is prepared as indicated in 5. above, starting from ethyl 2-hydroxy-3-[1-(1H-imidazol-4-yl)pentyl]-benzoate (prepared in Example 1.A.3.). The residue obtained after evaporation of the solvent is dissolved in a 2.5N ethanolic solution of hydrochloric acid. The 2-hydroxy-3-[1-(1H-imidazol-4-yl)pentyl]-benzamide hydrochloride separates after addition of diethyl ether. Yield: 50%.
NMR (DMSO): delta 0.83(3H,t), 1.08 to 1.34(4H,m), 3.3 to 3.5(2H,m), 4.44(1H,t), 6.82(1H,t), 7.37 to 7.40(2H,s+d), 7.82(1H,d), 8.97(1H,s).

The following compounds have been prepared in the same way:

16. 2-hydroxy-3-[(1H-imidazol-4-yl)methyl]-N,N-dimethylbenzamide.
M.P.: 208° C.

| Analysis for $C_{13}H_{16}N_3O_2$ in %: | | | |
|---|---|---|---|
| calc. | C 63.67 | H 6.12 | N 17.14 |
| found: | 63.58 | 6.06 | 17.09 |

17. 2-hydroxy-N-(2-hydroxyethyl)-3-[(1H-imidazol-4-yl)methyl]-benzamide hydrochloride.
M.P.: 200.6° C.

| Analysis for $C_{13}H_{15}N_3O_3 \cdot HCl$ in %: | | | |
|---|---|---|---|
| calc. | C 52.44 | H 5.38 | N 14.12 |
| found | 52.49 | 5.36 | 13.98 |

EXAMPLE 5. PREPARATION OF THE 1-(1H-IMIDAZOL-4-YL)ALKYL-BENZAMIDES OF FORMULA I BY REACTION OF THE ACIDS OF FORMULA IV WITH A NITROGEN COMPOUND OF FORMULA III.

1. 3-[(1H-imidazol-4-yl)methyl]-2-methoxybenzamide hydrochloride. A suspension of 3.1 g (13.4 mmoles) of 3-[(1H-imidazol-4-yl)methyl]-2-methoxybenzoic acid (prepared in Example 2.B.1) and 4.06 g (40.2 mmoles) of triethylamine, in 30 ml of dry dichloromethane, is cooled to 0° C. 4.36 g (40.2 mmoles) of ethyl chloroformate in solution in 10 ml of dry dichoromethane are added thereto. After this addition, the mixture is stirred further for half an hour at 0° C., and then for another half an hour at ambient temperature. A stream of gaseous ammonia, dried over potassium hydroxide, is then passed through the reaction mixture for one night. The mixture is then heated under reflux for half an hour, the solvent is evaporated under reduced pressure, and the residue is purified by chromatography on silica gel (eluent: 89:10:1 v/v/v dichloromethane-methanol-ammonia). 2.9 g of 3-[(1H-imidazol-4-yl)methyl]-2-methoxybenzamide, which crystallizes from acetonitrile, are obtained. Yield: 95%.
The amide, treated with 1.2 equivalent of hydrochloric acid in ethanol, is converted into the hydrochloride. M.P.: 160.5° C. (isopropyl alcohol).

| Analysis for $C_{12}H_{13}N_3O_2 \cdot HCl$ in %: | | | |
|---|---|---|---|
| calc. | C 53.84 | H 5.27 | N 15.73 |
| found | 53.94 | 5.30 | 15.81 |

The following compound has been prepared in the same way:

2. 3-[(1H-imidazol-4-yl)methyl]-2-n-propoxybenzamide. This compound is prepared from 3-[1H-imidazol-4-yl)methyl]-2n-propoxybenzoic acid (prepared in Example 2.B.2.) with a yield of 52%. M.P.: 161° C.

| Analysis for $C_{14}H_{17}N_3O_2$ in %: | | | |
|---|---|---|---|
| calc. | C 64.86 | H 6.56 | N 16.22 |
| found | 64.93 | 6.60 | 16.14 |

EXAMPLE 6. PREPARATION OF THE 1-(1H-IMIDAZOL-4-YL)ALKYL-BENZAMIDES OF FORMULA I BY HYDROLYSIS OF THE 2-HYDROXY-3-[1-(1H-IMIDAZOL-4-YL)ALKYL]-BENZONITRILES OF FORMULA V.

1. 2-hydroxy-3-[(1H-imidazol-4-yl)methyl]-benzamide. 13.1 g (66 mmoles) of 2-hydroxy-3-[(1H-imidazol-4-yl)methyl]-benzonitrile (prepared in Example 3.1.) are stirred in 50 ml of a 80% by volume aqueous solution of sulfuric acid, until solution is complete. The mixture is then heated at 65° C. for 3 hours. The reaction mixture is poured on ice and neutralized with sodium bicarbonate. It is then filtered and the filtrate is extracted several times with ethyl acetate. The organic phases are washed with a saturated aqueous solution of sodium chloride, dried over sodium sulfate and evaporated under reduced pressure. The residue is purified by chromatography on silica gel (eluent: 84:15:1 v/v/v dichloromethane-methanol-ammonia). There are obtained 9.8 g of 2-hydroxy-3-[(1H-imidazol-4-yl)methyl]-benzamide, which compound is identical with that obtained in Example 4.1. Yield: 68%.

2. 2-hydroxy-3-[1-(1H-imidazol-4-yl)ethyl]-benzamide. A suspension of 1.07 g (5 mmoles) of 2-hydroxy-3-[1-(1H-imidazol-4-yl)ethyl]-benzonitrile (prepared in Example 3.2.) in 4 ml of a 80% by volume aqueous solution of sulfuric acid, is stirred at 65° C. for 3 hours. The reaction mixture is then poured on ice, neutralized with sodium bicarbonate and extracted several times with ethyl acetate. The organic phases are dried over sodium sulfate and the solvent is evaporated under reduced pressure. The residue is taken up in 50 ml of a 6N aqueous solution of hydrochloric acid and neutralized with a 1N aqueous solution of sodium hydroxide. The precipitate which separates is filtered off, washed with water and with diethyl ether and dried under reduced pressure. 0.7 g of practically pure 2-hydroxy-3-[1-(1H-imidazol-4-yl)ethyl]-benzamide is obtained. Yield: 70%.
The hydrochloride of the compound obtained is identical with that prepared in Example 4.5.

3. 2-hydroxy-3-[(1H-imidazol-4-yl)methyl]-benzamide hydrochloride. 2 g of 2-hydroxy-3-[(1H-imidazol-4-yl)methyl]-benzonitrile (prepared in Example 3.1.) and 4 ml of water are added to 40 ml of methanol previously saturated at −10° C. with a stream of gaseous hydrogen chloride. The mixture is stirred at ambient temperature for 24 hours. The solution is then concentrated under reduced pressure and the residue is heated at 75° C. for 3 hours. The latter is then recrystallized twice from water. There are obtained 1.5 g of 2-hydroxy-3-[(1H-imidazol-4-yl)methyl]-benzamide hydrochloride, which is identical with the compound obtained in Example 4.1. Yield: 59%.

We claim:

1. A compound selected from the group consisting of substituted 1-(1H-imidazol-4-yl)alkyl-benzamide, the optically active isomers thereof and racemic mixtures thereof, of the formula

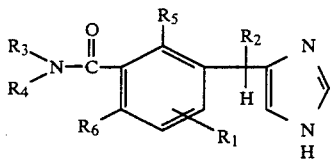 (I)

wherein
$R_1$ and $R_2$ each, independently, represent a hydrogen atom or an alkyl radical,
$R_3$ represents a hydrogen atom, an alkyl or hydroxyalkyl radical, an amino or hydroxyl group,
$R_4$ represents a hydrogen atom or an alkyl radical, or
$R_3$ and $R_4$, taken together with the nitrogen atom to which they are attached, represent a heterocyclic radical selected from the group consisting of the pyrrolidino, piperidino and morpholino radicals, and
$R_5$ and $R_6$ each, independently, represent a hydrogen atom, a hydroxyl group, an alkyl or alkoxy radical,
at least one of the symbols $R_5$ and $R_6$ being other than a hydrogen atom,
all the alkyl and alkoxy radicals having 1 to 4 carbon atoms,
or a non-toxic pharmaceutically acceptable acid addition salt thereof.

2. A compound as claimed in claim 1, namely 2-hydroxy-3-[(1H-imidazol-4-yl)methyl]-benzamide or a non-toxic, pharmaceutically acceptable acid addition salt thereof.

3. A compound as claimed in claim 1, namely 2-hydroxy-3-[1-(1H-imidazol-4-yl)ethyl]-benzamide or a non-toxic, pharmaceutically acceptable acid addition salt thereof.

4. A compound as claimed in claim 1, namely 2-hydroxy-3-[(1H-imidazol-4-yl)methyl]-N-methylbenzamide or a non-toxic, pharmaceutically acceptable acid addition salt thereof.

5. A compound as claimed in claim 1, namely 2,6-dihydroxy-3-[(1H-imidazol-4-yl)methyl]-benzamide or a non-toxic, pharmaceutically acceptable acid addition salt thereof.

6. A compound as claimed in claim 1, namely 2-hydroxy-3-[(1H-imidazol-4-yl)methyl]-6-methylbenzamide or a non toxic, pharmaceutically acceptable acid addition salt thereof.

7. A compound as claimed in claim 1, namely 2-hydroxy-5-[(1H-imidazol-4-yl)methyl]-benzamide or a non-toxic, pharmaceutically acceptable acid addition salt thereof.

8. A compound as claimed in claim 1, namely 2-hydroxy-3-[(1H-imidazol-4-yl)methyl]-benzohydrazide or a non-toxic, pharmaceutically acceptable acid addition salt thereof.

9. A compound as claimed in claim 1, namely dextrorotatory (+)-2-hydroxy-3-[1-(1H-imidazol-4-yl)ethyl]-benzamide or a non-toxic, pharmaceutically acceptable acid addition salt thereof.

10. A pharmaceutical composition comprising a therapeutically effective amount of a substituted 1-(1H-imidazol-4-yl)alkyl-benzamide as claimed in claim 1 and a pharmaceutically acceptable solid or liquid diluent or carrier therefor.

11. A method for achieving an anti-ischemic effect in a patient in need thereof, which comprises administering to said patient an effective amount of a substituted 1-(1H-imidazol-4-yl)alkyl-benzamide as claimed in claim 1.

12. A method of producing $\alpha_2$-adrenergic receptor agonist activity in a patient in need thereof, which comprises administering to said patient an amount effective to produce said activity of a substituted 1-(1H-imidazol-4-yl)alkyl-benzamide as claimed in claim 1.

* * * * *